United States Patent
Trieu

(10) Patent No.: US 9,895,190 B2
(45) Date of Patent: Feb. 20, 2018

(54) DEVICES AND METHODS FOR RADIOFREQUENCY ABLATION HAVING AT LEAST TWO ELECTRODES

(71) Applicant: Warsaw Orthopedic, Inc., Warsaw, IN (US)

(72) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 911 days.

(21) Appl. No.: 14/263,620

(22) Filed: Apr. 28, 2014

(65) Prior Publication Data

US 2015/0305801 A1 Oct. 29, 2015

(51) Int. Cl.
*A61B 18/14* (2006.01)
*A61B 18/00* (2006.01)

(52) U.S. Cl.
CPC ........ *A61B 18/148* (2013.01); *A61B 18/1477* (2013.01); *A61B 2018/0044* (2013.01); *A61B 2018/00285* (2013.01); *A61B 2018/00565* (2013.01); *A61B 2018/1435* (2013.01); *A61B 2018/1475* (2013.01)

(58) Field of Classification Search
CPC ... A61B 18/14; A61B 18/1477; A61B 18/148; A61B 18/1482; A61B 2018/1407; A61B 2018/1425; A61B 2018/1427; A61B 2018/143; A61B 2018/1475; A61B 2018/1432; A61B 2018/1435; A61B 2018/144; A61B 2018/0044; A61B 2018/00565

USPC ................ 606/41, 45–50; 607/117
See application file for complete search history.

(56) References Cited

U.S. PATENT DOCUMENTS

| | | |
|---|---|---|
| 5,147,355 A | 9/1992 | Friedmann et al. |
| 5,334,181 A | 8/1994 | Rubinsky et al. |
| 5,520,682 A | 5/1996 | Baust et al. |
| 5,906,612 A | 5/1999 | Chinn |
| 6,032,675 A | 3/2000 | Rubinsky |
| 6,179,831 B1 | 1/2001 | Bliweis |
| 6,190,378 B1 | 2/2001 | Jarvinen |
| 6,485,422 B1 | 11/2002 | Mikus et al. |
| 6,579,287 B2 | 6/2003 | Wittenberger et al. |
| 6,672,095 B1 | 1/2004 | Luo |
| 6,761,715 B2 | 7/2004 | Carroll |
| 6,789,545 B2 | 9/2004 | Littrup et al. |
| 6,796,979 B2 | 9/2004 | Lentz |
| 6,902,547 B2 | 6/2005 | Aves et al. |
| 6,926,711 B2 | 8/2005 | Lentz et al. |
| 7,381,208 B2 | 6/2008 | van der Walt et al. |
| 7,510,554 B2 | 3/2009 | Duong et al. |

(Continued)

FOREIGN PATENT DOCUMENTS

WO 2010102310 A2 9/2010

*Primary Examiner* — Thomas Giuliani

(57) ABSTRACT

Various embodiments are described herein for an extendable electrode configured to receive and conduct radiofrequency discharges for heating a target tissue site, a device for deploying the extendable electrode, and an apparatus for deploying the extendable electrode. Methods for use of the device and apparatus in radiofrequency ablation are described. In various embodiments, the extendable electrode is a coil electrode. Embodiments are described wherein the electrode, device, apparatus, and methods provide radiofrequency ablation treatment of intervertebral discs.

14 Claims, 16 Drawing Sheets

(56) References Cited

U.S. PATENT DOCUMENTS

| | | | |
|---|---|---|---|
| 7,625,368 B2 | 12/2009 | Schechter et al. | |
| 7,641,679 B2 | 1/2010 | Joye et al. | |
| 7,846,154 B2 | 12/2010 | Bliweis et al. | |
| 7,938,822 B1 | 5/2011 | Berzak et al. | |
| 7,967,814 B2 | 6/2011 | Levin | |
| 7,967,815 B1 | 6/2011 | Berzak et al. | |
| 8,083,733 B2 | 12/2011 | Toubia et al. | |
| 8,162,812 B2 | 4/2012 | Shai et al. | |
| 2002/0068964 A1 | 6/2002 | Dobak | |
| 2004/0049177 A1 | 3/2004 | Zvuloni et al. | |
| 2005/0085807 A1* | 4/2005 | Venturelli | A61B 18/1477 606/41 |
| 2005/0177215 A1 | 8/2005 | Rosenberg | |
| 2005/0240239 A1 | 10/2005 | Boveja et al. | |
| 2007/0021745 A1* | 1/2007 | McIntyre | A61B 18/1477 606/41 |
| 2007/0156125 A1 | 7/2007 | DeLonzor | |
| 2007/0191732 A1 | 8/2007 | Voegele | |
| 2008/0306475 A1 | 12/2008 | Lentz et al. | |
| 2009/0036823 A1 | 2/2009 | LePirvert | |
| 2009/0192505 A1 | 7/2009 | Askew et al. | |
| 2009/0299357 A1 | 12/2009 | Zhou | |
| 2010/0168739 A1 | 7/2010 | Wu et al. | |
| 2010/0179527 A1 | 7/2010 | Watson et al. | |
| 2010/0292764 A1 | 11/2010 | Soomro et al. | |
| 2011/0071515 A1* | 3/2011 | Faure | A61B 18/1206 606/33 |
| 2011/0270238 A1 | 11/2011 | Rizq et al. | |
| 2011/0313411 A1 | 12/2011 | Anderson et al. | |
| 2012/0046531 A1 | 2/2012 | Hua | |
| 2012/0065630 A1 | 3/2012 | Berzak et al. | |
| 2012/0089047 A1 | 4/2012 | Ryba et al. | |
| 2012/0109116 A1 | 5/2012 | Asconeguy et al. | |
| 2012/0253336 A1 | 10/2012 | Littrup et al. | |
| 2015/0305799 A1* | 10/2015 | Trieu | A61B 18/1477 606/41 |
| 2015/0305800 A1* | 10/2015 | Trieu | A61B 18/1477 606/41 |

* cited by examiner

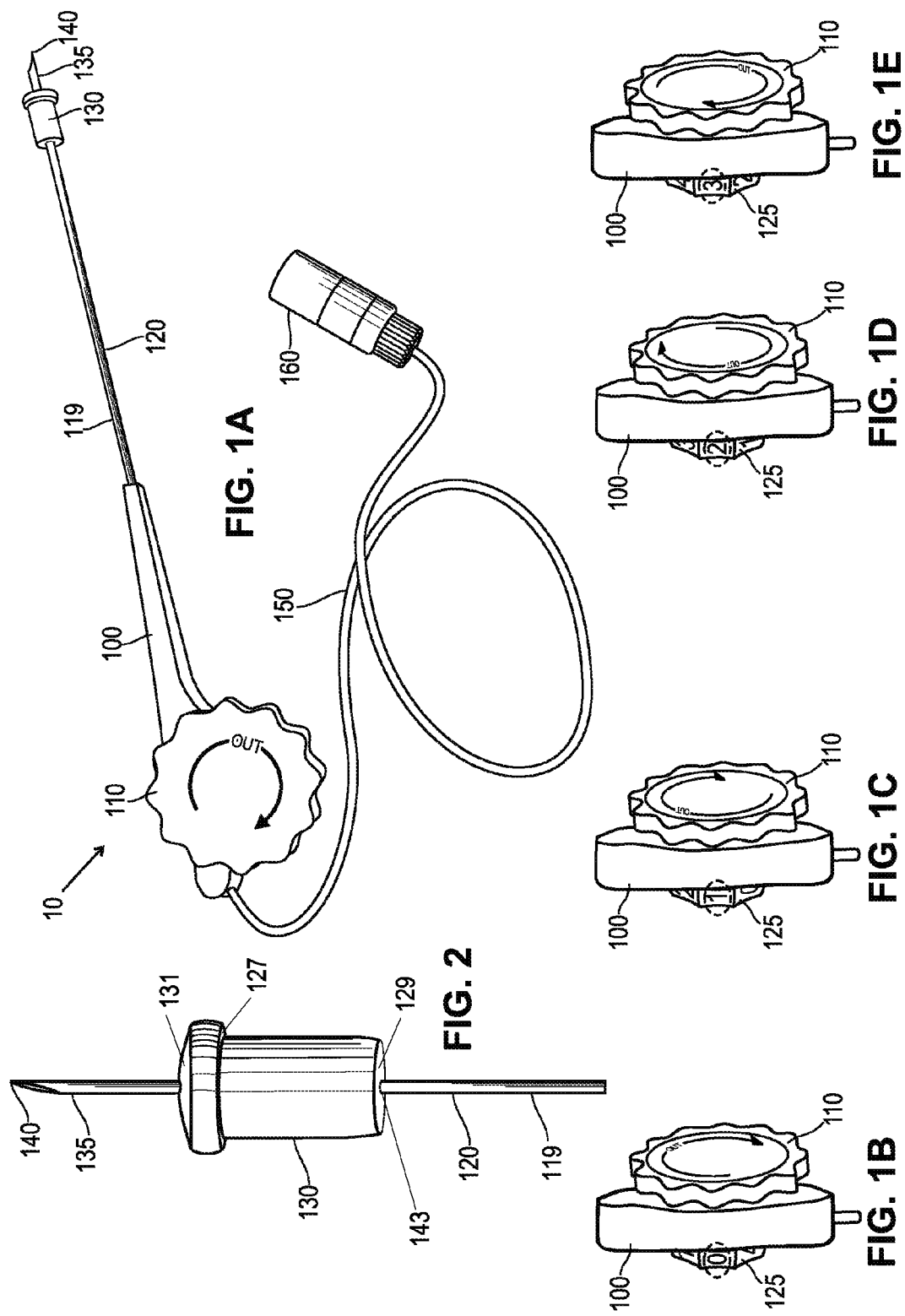

DEVICES AND METHODS FOR RADIOFREQUENCY ABLATION HAVING AT LEAST TWO ELECTRODES

FIELD

The present disclosure relates generally to devices and methods for providing radiofrequency ablation.

BACKGROUND

Acute and chronic pain management has been a concern for as long as medicine has been practiced. Several methods of inducing analgesia and anesthesia have been developed. For example, the use of chemical substances is perhaps the most common approach to pain relief which requires suitable substances that are effective, safe to humans, and do not cause complications or abnormal reactions. Despite the great advances that have been made in the field of anesthesiology, and in the field of pain relief in general, there are still some drawbacks to chemical-based approaches.

Radiofrequency (RF) ablation is a technique that has been used in a variety of medical contexts including treatments for cancer and pain relief. During radiofrequency (RF) ablation, current passing through tissue from an active electrode leads to ion agitation, which is converted by means of friction into heat. The process of cellular heating causes coagulation necrosis and consequent cell death. Because ion agitation, and thus tissue heating, is greatest in areas of highest current density (e.g., closest to the active electrode tip), necrosis is limited to a relatively small volume of tissue surrounding the RF electrode. RF ablation, therefore, can be used as an effective treatment of cancer or can be used to selectively ablate unwanted nerve tissue to alleviate and/or reduce pain.

Some painful conditions involve intervertebral disc abnormalities, which have a high incidence in the population. Intervertebral discs are complex structures with dynamic properties resulting from the interaction of a central, gelatinous nucleus pulposus surrounded by a tough, fibrous, semielastic annulus fibrosus. Intervertebral discs may be displaced or damaged due to disease or aging. Disruption of the annulus fibrosus can allow the nucleus pulposus to protrude into the vertebral canal or intervertebral foramen, a condition known as a herniated or slipped disc. A rupture in the annulus fibrosus can allow the escape of nucleus pulposus components. The extruded nucleus pulposus may press on a spinal nerve, which may result in nerve damage, pain, numbness, muscle weakness and paralysis. Furthermore, as a disc dehydrates and hardens due to age or disease, the disc space height will be reduced, leading to instability of the spine, decreased mobility and pain. Moreover, excessive movement of the spinal segments caused by the disc space height reduction could weaken the annulus fibrosus and in certain cases, tear it.

Therefore, there is a need for new ablation devices and methods that effectively ablate a target tissue area. New ablation devices and methods that allow safer and more effective treatments of various intervertebral disc abnormalities such as hernias, tears or bulges in the annulus fibrosus are also needed.

SUMMARY

There is a need for devices and methods that enable medical practitioners to more effectively focus and control the range of radiofrequency (RF) ablation treatment over wider volumes and provide safe treatments. One concern with respect to current RF ablation techniques is that health care practitioners may have difficulty positioning the electrode, often in the form of a tip, of the device in a location to get optimal, consistent, and well targeted clinical results over a sufficient range. This may also result in unwanted necrosis of adjacent tissue, or conversely, lack of coverage of affected areas, which can lead to clinical adverse events.

Accordingly, there is a need for devices and methods that provide efficient ablation of nerve and soft tissue with increased areas of coverage under improved control by medical practitioners. Ablating a larger surface area, while minimizing destruction of tissue that should not be destroyed, are achieved by various embodiments of the devices and methods disclosed herein. These advantages, described in further detail, fulfill a particularly strong need in the area of treating spinal disc pathologies such as hernias, bulges, and fissures.

Ablation devices and methods are provided that allow for monitoring and control of temperature, pressure and position of ablating probes to achieve a more precise destruction of the nerve tissue and other soft tissue in a minimally invasive procedure. The ablation devices, apparatus, and methods provided herein allow the electrode of the device to be easily positioned in an optimal location to obtain improved ablation with minimal unwanted destruction to adjacent nerve and/or soft tissue.

In some embodiments, there is a device for providing radiofrequency current to a target tissue site, the device comprising: a cannula having a proximal end and a distal end and a longitudinal axis therebetween, the distal end comprising a tip; a first electrode configured to conduct and discharge radiofrequency current for heating the target tissue site, the first electrode disposed within the cannula and having a retracted position within the longitudinal axis of the cannula and a deployed position outside the tip of the cannula; an adjustment member disposed at or near the proximal end of the cannula, the adjustment member configured to engage the first electrode in the retracted position or the deployed position; a second electrode disposed within the cannula and configured to conduct and discharge radiofrequency for heating the target tissue site; and an insulation material disposed about the first electrode and configured to reduce or prevent conduction of radiofrequency current in the cannula.

In some embodiments, there is an apparatus for providing radiofrequency current to heat a target tissue site, the apparatus comprising: a device housing; an cannula engaged at a distal end of the device housing, the cannula having a proximal end and a distal end and a longitudinal axis therebetween, the distal end comprising a needle tip; a radiofrequency electrode for heating a target tissue site, the radiofrequency electrode comprising a distal end and a proximal end, the distal end configured to be placed into the cannula and configured to become a coiled region when urged out of the cannula, the proximal end configured to contact or be coupled to a radiofrequency source; a needle stopper disposed around a portion of the longitudinal axis of the cannula and having a larger diameter than the diameter of the cannula, the needle stopper configured to prevent select longitudinal movement of the cannula beyond a discrete position; and an electrical connection assembly configured to electrically couple the radiofrequency electrode to a radiofrequency power source.

In some embodiments the adjustment member can selectively extend, expand, or retract a coiled region of the RF electrode from the lumen of the cannula at or near the target tissue site. In some embodiments, the adjustment member can comprise a switch or a dial configured to extend or expand the coil to a selected length. In some embodiments, a switch or dial can be moved clockwise or counterclockwise to engage the electrode to extend or retract the coiled region.

In some embodiments, there is a method of providing radiofrequency treatment to an intervertebral disc, the disc comprising a nucleus pulposus, an annulus fibrosus, the method comprising: inserting an cannula having a needle tip up to the annulus fibrosus to penetrate the disc annulus and enter the nucleus pulposus, determining the correct depth of needle tip penetration using fluoroscopy or by a needle stopper disposed on the needle tip to prevent insertion beyond a target tissue site; extending a radiofrequency electrode from the needle tip to form a coil of the radiofrequency electrode within the nucleus pulposus adjacent to a target ablation site; and activating the radiofrequency electrode to deliver radiofrequency energy to the ablation site.

In some embodiments, devices and methods for destroying nerves and other soft tissue via a minimally invasive procedure to alleviate pain are also provided. Destruction of the target nerve or soft tissue can eliminate and/or reduce pain symptoms.

In some embodiments, a needle tip through which the RF electrode extends is moved or rotated to expose additional areas for additional RF heating. In some embodiments, after RF ablation is complete, or sufficient to fulfill the therapeutic needs, the RF electrode is retracted and then the RF needle tip is removed from the disc. The RF needle can then be removed from a patient undergoing treatment.

In some embodiments, the device or apparatus for providing radiofrequency ablation can comprise a computer system. In some embodiments, the computer system is coupled to the device or apparatus for providing radiofrequency ablation. The computer system can be programmed with software adapted to receive real time or retrospective time data from a monitoring device and/or at least one imaging device in order to calculate optimal temperatures and positions, and other parameters for the radiofrequency electrode tailored to the area subjected to ablation.

The RF device, apparatus, and methods disclosed herein can be used in a variety of procedures, surgical (open, mini-open, minimally invasive surgery), with retractors, through a cannula, percutaneously, and/or through small-gauge (e.g., 8 to 18 gauge) access needles. In various embodiments, any approach and/or trajectories, including posterior, posterolateral, lateral, anterolateral, and/or anterior, to the intervertebral discs, can be used with the RF device, apparatus, and methods disclosed herein.

In some embodiments, a thermocouple, or other type of temperature sensor, is included near the needle tip to measure and monitor tissue temperature. In some embodiments, the temperature is constantly monitored and displayed on a generator, controller or other display mechanism. In some embodiments, the temperature sensor can be located or positioned in a similar manner as described for a return or second electrode. In various embodiments additional electrodes can be used including arrays of electrode. In some embodiments, a medical practitioner can make use of the temperature read-out to properly control the RF heating of tissues. In various embodiments, open-loop or closed-controlled heating can be used depending on the capability of the generator, controller or other such device.

In other embodiments, a computer connected to the at least one ablation device, monitoring device, and/or imaging device can also be provided, the computer programmed with software for accepting input from the at least one monitoring device and/or imaging device is configured to compute an optimal temperature for a deployed radiofrequency ablation electrode. There are a variety of advantages provided by the various embodiments disclosed herein. Extendable and/or expandable electrodes enable ablation of large volumes. In the context of some embodiments such as treatments directed to regions of the disc nucleus of intervertebral discs, the capability of covering wider and regions of the disc with more accuracy, as disclosed in various embodiments herein, is particularly of value to medical practitioners. Various embodiments disclosed herein provide for the use of small diameter RF needles, for example, 8 to 18 gauge needles, in treatments of intervertebral discs. Smaller diameter can minimize damage to the disc annulus during needle insertion and treatment and reduce the potential for subsequent disc degeneration and rehemiation. A retractable electrode facilitates removal of the radiofrequency device in a small profile and thus minimizes damage to the disc annulus. The devices and methods disclosed herein can be used in both minimally invasive spine surgery (MIS) and percutaneous disc decompression procedures. In various embodiments an inflatable needle stopper can maintain a predetermined depth of penetration to avoid unwanted ablation and improve patient safety.

In some embodiments, there is a device for providing radiofrequency current to a target tissue site that comprises an inflatable anchor member. In some embodiments of the device comprising the inflatable anchor member, the device comprises a cannula having a proximal end and a distal end and a longitudinal axis therebetween, the distal end comprising a tip; a first electrode configured to conduct and discharge radiofrequency current for heating the target tissue site, the first electrode disposed within the cannula and having a refracted position within the longitudinal axis of the cannula and a deployed position outside the tip of the cannula; an adjustment member disposed at or near the proximal end of the cannula, the adjustment member configured to engage the first electrode in the retracted position or the deployed position; and an inflatable anchor member disposed around a portion of the longitudinal axis of the cannula and when inflated having a larger diameter than the diameter of the cannula and being configured to anchor the cannula tip at a desired position and/or location, and means for inflating the inflatable anchor member.

In some embodiments, the device comprising the inflatable anchor member further comprises a second electrode disposed within the cannula and configured to conduct radiofrequency away from the target tissue site.

In some embodiments, the device comprising the inflatable anchor member further comprises an insulation material disposed about the first electrode and configured to reduce or prevent conduction of radiofrequency current in the cannula.

In some embodiments of the device comprising the inflatable anchor member the first electrode is disposed parallel to the second electrode and the insulation material is disposed between the first and second electrode along the longitudinal axis of the cannula.

In some embodiments of the device comprising the inflatable anchor member the means for inflating the inflatable anchor member comprises an inflator and an inflation lumen in fluid communication with the inflator and the inflatable anchor member. In some embodiments, the inflator is a bulb or a syringe. In some embodiments, the inflation lumen is disposed within the cannula.

In some embodiments of the device comprising the inflatable anchor member the adjustment member is configured to engage the first electrode and selectively move it in the deployed position outside of the tip of the cannula and the retracted position inside the cannula by rotational movement of the adjustment member relative to the cannula.

In some embodiments of the device comprising the inflatable anchor member (i) the cannula comprises a cooling channel configured to cool the first and/or second electrode; or (ii) the cannula further comprises a thermocouple disposed adjacent to the tip.

In some embodiments of the device comprising the inflatable anchor member, the first electrode comprises a helical portion when deployed within an intervertebral disc to ablate a portion of an annulus fibrosus and/or nucleus pulposus of the intervertebral disc.

In some embodiments, there is an apparatus for providing radiofrequency current to heat a target tissue site that comprises an inflatable anchor member. In some embodiments of the apparatus for providing radiofrequency current to heat a target tissue site that comprises an inflatable anchor member, the apparatus comprises a device housing; a cannula engaged at a distal end of the device housing, the cannula having a proximal end and a distal end and a longitudinal axis therebetween, the distal end comprising a needle tip; a radiofrequency electrode for heating a target tissue site, the radiofrequency electrode comprising a distal end and a proximal end, the distal end configured to be placed into the cannula and configured to become a coiled region when urged out of the cannula, the proximal end configured to contact or be coupled to a radiofrequency source; an inflatable anchor member disposed around a portion of the longitudinal axis of the cannula and when inflated having a larger diameter than the diameter of the cannula and being configured to anchor the cannula tip at a desired position and/or location; an inflator; an inflation lumen defined in fluid communication with the inflator and the inflatable anchor member; and an electrical connection assembly configured to electrically couple the radiofrequency electrode to a radiofrequency power source.

In some embodiments of the apparatus for providing radiofrequency current to heat a target tissue site that comprises an inflatable anchor member the inflator is a bulb or a syringe.

In some embodiments of the apparatus for providing radiofrequency current to heat a target tissue site that comprises an inflatable anchor member the inflation lumen is disposed within the cannula.

In some embodiments of the apparatus for providing radiofrequency current to heat a target tissue site that comprises an inflatable anchor member the proximal end of the radiofrequency electrode engages an adjustment member to selectively extend, expand, or retract the coiled region from the cannula at or near the target tissue site.

In some embodiments of the apparatus for providing radiofrequency current to heat a target tissue site that comprises an inflatable anchor member, the apparatus further comprises a return electrode.

In some embodiments of the apparatus for providing radiofrequency current to heat a target tissue site that comprises an inflatable anchor member the apparatus further comprises an insulation material disposed between the radiofrequency electrode and the return electrode.

In some embodiments of the apparatus for providing radiofrequency current to heat a target tissue site that comprises an inflatable anchor member the return electrode is disposed within the cannula.

In some embodiments of the apparatus for providing radiofrequency current to heat a target tissue site that comprises an inflatable anchor member, the apparatus further comprises a thermocouple disposed adjacent to the needle tip and a generator/controller for monitoring the temperature from the thermocouple.

In some embodiments there is a method of providing radiofrequency treatment to an intervertebral disc of a patient, the disc comprising an annulus fibrosus, that comprises providing a device comprising an cannula having a proximal end and a distal end and a longitudinal axis therebetween, the distal end comprising a needle tip; a radiofrequency electrode for heating a target tissue site, the radiofrequency electrode comprising a distal end and a proximal end, the distal end configured to be placed into the cannula and configured to become a coiled region when urged out of the cannula, the proximal end configured to contact or be coupled to a radiofrequency source; an inflatable anchor member disposed around a portion of the longitudinal axis of the cannula and when inflated having a larger diameter than the diameter of the cannula and being configured to anchor the cannula tip at a desired location and/or depth; an inflator, and an inflation lumen defined in fluid communication with the inflator and the inflatable anchor member; inserting the cannula up to a desired location and/or depth of the annulus fibrosus; inflating the inflatable anchor member to anchor the cannula tip at the desired location and/or depth; extending the radiofrequency electrode to a desired region of tissue for treatment; and activating the radiofrequency electrode to apply radiofrequency energy for a sufficient time to provide radiofrequency treatment to the intervertebral disc. In some embodiments, the method further comprises a return electrode.

In some embodiments there is a device for providing radiofrequency current to a target tissue site wherein the device comprises a first and second electrode. In some embodiments the device for providing radiofrequency current to a target tissue site wherein the device comprises a first and second electrode comprises a cannula having a proximal end and a distal end and a longitudinal axis therebetween, the distal end comprising a tip; a first electrode configured to conduct and discharge radiofrequency current for heating the target tissue site, the first electrode disposed within the cannula and having a retracted position within the longitudinal axis of the cannula and a deployed position outside the tip of the cannula, the first electrode configured to become a coiled region when urged out of the cannula; a second electrode; an adjustment member disposed at or near the proximal end of the cannula, the adjustment member configured to engage the first electrode and/or the second electrode to move the first and/or second electrode from retracted positions to and from deployed positions; and an insulation material.

In some embodiments of the device for providing radiofrequency current to a target tissue site wherein the device comprises a second electrode the second electrode is in a bipolar arrangement with the first electrode.

In some embodiments of the device for providing radiofrequency current to a target tissue site wherein the device comprises a second electrode the second electrode is disposed within the cannula.

In some embodiments of the device for providing radiofrequency current to a target tissue site wherein the device comprises a second electrode the second electrode is configured to conduct radiofrequency away from the target tissue site.

In some embodiments of the device for providing radiofrequency current to a target tissue site wherein the device comprises a second electrode the insulation material is disposed between the first electrode and the second electrode and configured to reduce or prevent conduction of radiofrequency current in the cannula.

In some embodiments of the device for providing radiofrequency current to a target tissue site wherein the device comprises a second electrode the second electrode has a concentric tubing configuration and surrounds the first electrode.

In some embodiments of the device for providing radiofrequency current to a target tissue site wherein the device comprises a second electrode the second electrode is comprised of nitinol wire or other suitable flexible material known to persons of skill in the art.

In some embodiments of the device for providing radiofrequency current to a target tissue site wherein the device comprises a second electrode the second electrode is flexible and extendable beyond the tip of the distal end of the cannula and does not contact the first electrode.

In some embodiments of the device for providing radiofrequency current to a target tissue site wherein the device comprises a second electrode the surface of the second electrode is coated with an insulation material.

In some embodiments of the device for providing radiofrequency current to a target tissue site wherein the device comprises a second electrode the second electrode is flexible and extendible and the device further comprises a deflector in the wall of the cannula whereby the second electrode when engaged by the adjustment member is extended from the cannula at a position along the wall of the cannula and separate from the cannula tip region.

In some embodiments of the device for providing radiofrequency current to a target tissue site wherein the device comprises a second electrode the second electrode is rigid when urged from the cannula. The second electrode in this embodiment tends to take on a straight configuration.

In some embodiments of the device for providing radiofrequency current to a target tissue site wherein the device comprises a second electrode the second electrode is disposed within the cannula and is uninsulated near the cannula tip.

In some embodiments of the device for providing radiofrequency current to a target tissue site wherein the device comprises a second electrode the second electrode is configured to become a coil when extended beyond the cannula, the coil being disposed within the coil of the first electrode.

In some embodiments of the device for providing radiofrequency current to a target tissue site wherein the device comprises a second electrode the second electrode is disposed within the cannula at the proximal end of the cannula.

In some embodiments of the device for providing radiofrequency current to a target tissue site wherein the device comprises a second electrode the second electrode is in a spiral configuration surrounding the cannula.

In some embodiments of the device for providing radiofrequency current to a target tissue site wherein the device comprises a second electrode the second electrode is urged from the cannula is configured to become a coil smaller in size than the first electrode and configured to take a position away from the first electrode.

In some embodiments there is an apparatus for providing radiofrequency current to heat a target tissue site, the apparatus comprising a device housing; a cannula having a proximal end and a distal end and a longitudinal axis therebetween, the distal end comprising a tip; a first electrode configured to conduct and discharge radiofrequency current for heating the target tissue site, the first electrode disposed within the cannula and having a refracted position within the longitudinal axis of the cannula and a deployed position outside the tip of the cannula, the first electrode configured to become a coiled region when urged out of the cannula; a second electrode; an adjustment member disposed at or near the proximal end of the cannula, the adjustment member configured to engage the first electrode and/or the second electrode to move the first and/or second electrode from retracted positions to and from deployed positions; an insulation material; and an electrical connection assembly configured to electrically couple the first and/or second electrode to a radiofrequency power source. In some embodiments of the apparatus for providing radiofrequency current to heat a target tissue site, the second electrode is configured to conduct radiofrequency away from the target tissue site. In some embodiments, the first and second electrode are configured in a bipolar arrangement. In some embodiments, the insulation material is disposed between the first electrode and the second electrode and configured to reduce or prevent conduction of radiofrequency current in the cannula.

In some embodiments, there is a method of providing radiofrequency treatment to an intervertebral disc of a patient, the disc comprising an annulus fibrosus, comprising: providing a device for providing radiofrequency current to a target tissue site, the device comprising: a cannula having a proximal end and a distal end and a longitudinal axis therebetween, the distal end comprising a tip; a first electrode configured to conduct and discharge radiofrequency current for heating the target tissue site, the first electrode disposed within the cannula and having a retracted position within the longitudinal axis of the cannula and a deployed position outside the tip of the cannula, the first electrode configured to become a coiled region when urged out of the cannula; a second electrode; an adjustment member disposed at or near the proximal end of the cannula, the adjustment member configured to engage the first electrode and/or the second electrode to move the first and/or second electrode from retracted positions to and from deployed positions; and an insulation material; inserting the cannula up to a desired location and/or depth of the annulus fibrosus; extending the radiofrequency electrode to a desired region of tissue for treatment; and activating the first and/or second electrode to apply radiofrequency energy for a sufficient time to provide radiofrequency treatment to the intervertebral disc. In some embodiments, the second electrode is configured to conduct radiofrequency away from the target tissue site. In some embodiments, the second electrode is in a bipolar arrangement with the first electrode.

Other features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

In part, other aspects, features, benefits and advantages of the embodiments will be apparent with regard to the following description, appended claims, and accompanying drawings in which:

FIGS. 1A, 1B, 1C, 1D, and 1E illustrate a radiofrequency ablation device with a connector for connecting the device to an radiofrequency generator;

FIG. 2 illustrates an inflatable needle stopper disposed on the radiofrequency ablation cannula;

Figure 3E:
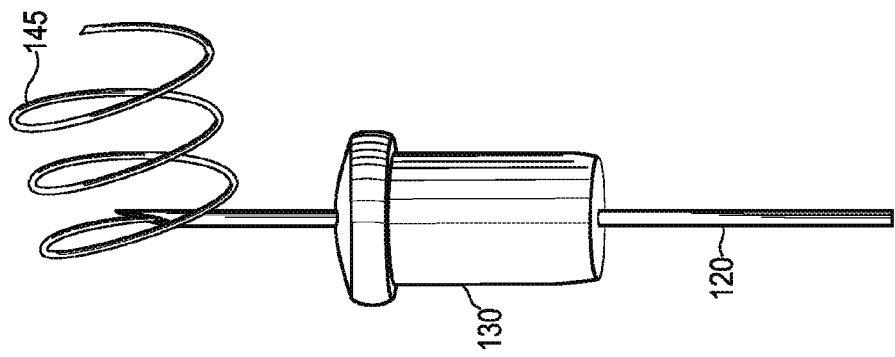
FIGS. 3A, 3B, 3C, 3D, and 3E illustrate the cannula with the radiofrequency electrode retracted or deployed at various stages of extension from the ablation cannula.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. The following description is presented to enable any person skilled in the art to make and use the present disclosure.

Devices and methods for efficient and precise radiofrequency ablation can be accomplished to ablate a target tissue site such as nerve, bone and soft tissue. The devices and methods provided can be used in a posterior approach or trajectory or a posterolateral approach or trajectory. In some embodiments, various percutaneous, non-percutaneous, minimally invasive surgical procedures and/or open surgical procedures can be used with the devices and methods disclosed herein.

Definitions

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward or distal end of the probe portion of the device that is described herein, and "rearward" or "proximal" (and forms thereof) means rearward or away from the direction of the forward, or distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", or the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments.

Radiofrequency Ablation

Radiofrequency (RF) ablation devices have been available to surgeons to treat many medical conditions, for example, in the treatment of tumors in lung, liver, kidney and other body organs. RF ablation has also been used for treatment of tumors, cardiac arrhythmias, chronic and post-operative pain, bone fractures and soft tissue wounds. Persons of skill in the art understand the level of heat production at an RF ablation electrode that will be effective to ablate different tissues or regions. As used herein, RF and radiofrequency are used interchangeably.

As used herein, the terms "radiofrequency electrode" and "RF electrode" are used interchangeably. The terms "radiofrequency electrode" and "RF electrode" refer to an electrode configured to receive and conduct radiofrequency energy and are configured to discharge radiofrequency energy to heat tissue to ablate it.

Radiofrequency ablation can be delivered to appropriate treatment sites inside a patient by a radiofrequency electrode or first electrode. In certain embodiments, the RF electrode can be introduced using a cannula or needle, or other introduction device having a size in the range of about 8-18 gauge. In some embodiments, a stopper can be used to maintain the proper distancing of the cannula or needle in the treatment of a target tissue site, such as for example, an intervertebral disc.

In some embodiments, the RF electrode contains a port for release of substance useful for navigation and/or monitoring. In some embodiments, the electrode can comprise a dual needle configured for ablation that can simultaneously monitor the temperature and/or pressure within the body of the patient.

Referring to FIGS. 1A-1E, shown therein is an example of an embodiment of a RF treatment device 10 for providing radiofrequency (RF) treatment. Generally, the RF treatment device 10 comprises a device housing 100, an adjustment member 110, a cannula 120 having a proximal end 119 and a distal end 135 and, not shown in FIG. 1, a radiofrequency electrode 145 also referred to as a first electrode (shown FIGS. 3A-3E) capable of being in a retracted state and an extended or deployed state wherein the radiofrequency electrode extends from the distal end 135 of the cannula 120 past needle tip 140. In some embodiments, the RF treatment device 10 comprises a device housing 100, an adjustment member 110, a cannula 120, a gauge 125, a needle stopper 130, a needle tip 140, an attachment cord or wire 150, and a connector 160 for connecting the RF treatment device 10 to a radiofrequency source.

In some embodiments, the tip 140 in FIG. 1A of the cannula 120 is pointed to allow for easy pushing through tissues. In some embodiments, the tip 140 of the cannula can be round or tapered. In various embodiments, the tip can be smooth for insertion. In some embodiments, the radiofrequency electrode 145 has a blunt tip such that the surgeon or health practitioner can eliminate any difficulty in positioning the electrode tip in the optimal location to get an optimal and consistent clinical result. The cannula 120 can house the first electrode and/or the second electrode.

FIGS. 1B-1E show a detailed view of the device housing 100, adjustment member 110, and gauge 125. Movement of the adjustment member correlates with changes in the how far the radiofrequency electrode extends from the distal end 135 of the cannula 120 and out of the needle tip 140. The adjustment member 110 is mounted to or attached to the RF treatment device 10. The gauge 125 indicates extension of the radiofrequency electrode 145 of FIGS. 3B-3E from the distal end 135 of the cannula 120 with, in some embodiments, larger numbers indicating a further extension of the radiofrequency electrode from the distal end 135 of the cannula 120. For example, rotation of the adjustment member 110 to the number one shown on the gauge 125 of FIG. 1C will cause the adjustment member to slidably engage the radiofrequency electrode 145 and cause it to slide out of the cannula to expose one coiled or helical region (FIG. 3B). The adjustment member 110 can slidably engage the radiofrequency electrode 145 and cause it to slide along the cannula's longitudinal axis. In this way, the radiofrequency electrode 145 can be in a retracted position within the cannula (shown as zero in FIG. 1B and not deployed or extended in FIG. 3A) or deployed where it is out of the cannula (shown in FIGS. 3B-3E). Likewise, rotation of the adjustment member 110 to the number two shown in FIG. 1D on the gauge 125 will cause the adjustment member to slidably engage the radiofrequency electrode 145 and cause it to slide along the longitudinal axis of the cannula and out of it to expose two coiled or helical regions (FIG. 3C).

Figure 3A:
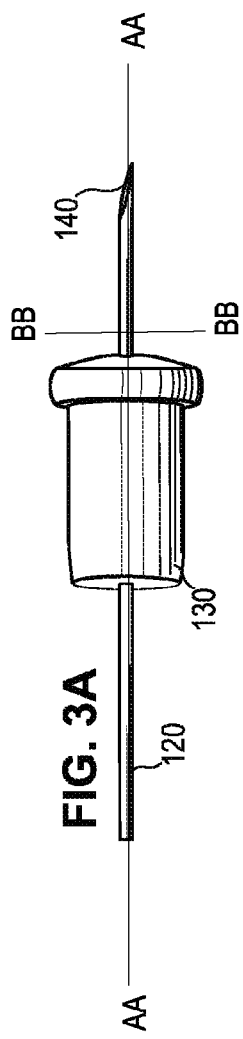
Figure 3B:
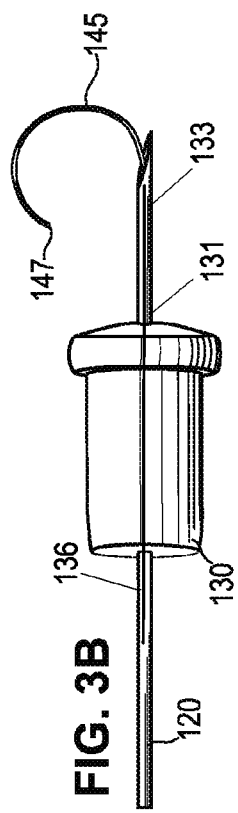
Figure 3C:
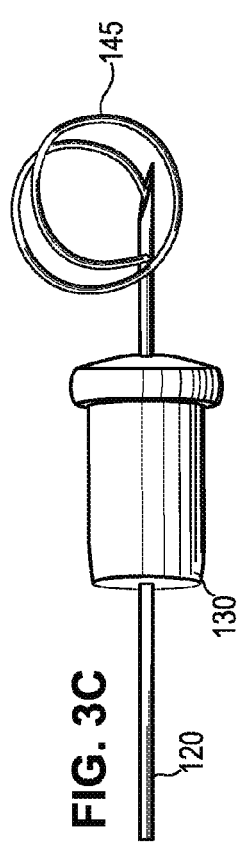
Figure 3D:
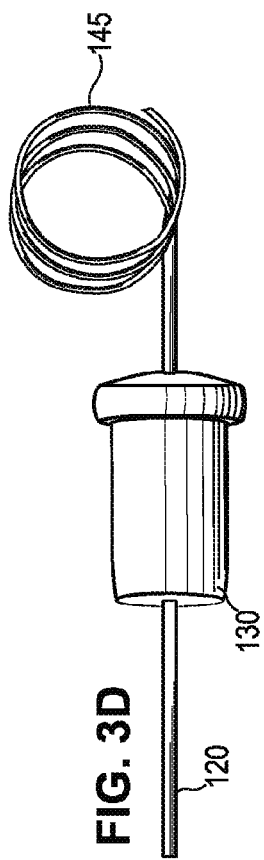

Rotation of the adjustment member 110 to the number three shown on the gauge 125 of FIG. 1E will cause the adjustment member to slidably engage the radiofrequency electrode 145 and cause it to slide along the longitudinal axis of the cannula and out of it to expose three coiled or helical regions (FIGS. 3D and 3E). The adjustment member 110 comprises, in this embodiment, a rotary dial or wheel that can be turned in a clockwise or counterclockwise direction. In other embodiments, other structures can be used, such as a knob or handle, and these other structures are within the understanding of persons of skill in the art.

The coil or helical region of the RF electrode in the deployed position allows for increased surface area for target tissue heating. The RF electrode can also heat the tissue in a more controlled manner and cause the desired necrosis of the tissue. The RF electrode can ablate the heat effective zone more evenly and in a controlled manner and the RF electrode can be extended and adjusted so as to focus the RF energy on the complete area and avoid ablating or charring unwanted tissue. In some embodiments, the radiofrequency discharged by the RF electrode can be from about 1-200 watts or from about 5-100 watts, or from about 25-50 watts.

To operably connect the adjustment member 110 and the radiofrequency electrode 145, a mechanical assembly disposed within the device housing 100 is configured to mechanically couple the adjustment member 110 and the radiofrequency electrode 145 so that a rotational movement of the adjustment member 110 will cause the longitudinal movement of the radiofrequency electrode 145 with respect to the cannula 120. For example, in FIG. 1 the adjustment member 110 can be used to deploy or retract the RF electrode 145, by applying a rotatable force that is generally perpendicular to the direction of insertion of the cannula 120 such as in a turning wheel arrangement with the electrode 145 which is generally flexible and connected to an inner spool of the adjustment member 110 that in this embodiment is shown as a wheel, or rotary dial.

In some embodiments, the device and methods provided comprise a stopper to avoid puncturing the end plates or the nerve. FIG. 2 shows a detailed view of the proximal end 119 and the distal end 135 of the cannula 120 with a needle stopper 130, and the needle tip 140. In some embodiments, the needle stopper 130 comprises an inflatable member. The inflatable member can be a balloon. The needle stopper 130 is disposed around a portion of the cannula 120. Its diameter is greater than the diameter of the cannula. In some embodiments, when the posterior approach is used for ablation at or near the intervertebral disc, if the cannula is pushed too far, it can puncture the nucleus pulposus, anterior annulus and/or the aorta, which can be detrimental to the patient. The stopper, in some embodiments, is disposed on or around the cannula and prevents or reduces the risk of puncturing these areas as it creates a physical barrier preventing puncture beyond the desired target tissue site.

In some embodiments as shown in FIG. 2, the needle stopper 130 is disposed transverse to the cannula 120 and it can be radially expanded. The needle stopper 130 can have a proximal end 129 and a distal end 131. Typically, the distal end comprises a diameter that is larger than the proximal end 129, however, this is not required. In some embodiments, the needle stopper can be tapered as it approaches a tissue contacting surface. In some embodiments, the needle stopper 130 can have a rim 127, which will act as a stopper at the tissue contacting surface so that the needle tip 140 cannot be pushed beyond a select point or a discrete region at or near the target tissue site. The needle stopper functions as a safety means to prevent the needle from penetrating an unwanted area of the tissue (e.g., nerve, blood vessel, etc.).

In some embodiments, the needle stopper 130 is immovably attached to the cannula 120 by attachment point 143. In other embodiments, the needle stopper is slidably attached to the cannula 120, however, movement is restricted as the diameter of the needle stopper is slightly larger than the cannula so that there is a snug fit, so that when the cannula is moved the needle stopper 130 will not be able to move unless an extreme pushing force is used to separate the needle stopper 130 from the cannula. In other embodiments, the needle stopper 130 can be slid on the cannula to a discrete region of it and then the needle stopper 130 can act to prevent further penetration of the cannula into an unwanted tissue area as the needle stopper will prevent the cannula from moving past the desired location at the target tissue site.

In some embodiments, when dealing with the intervertebral disc, the needle stopper 130 can be used with the posterior approach or trajectory for the non-percutaneous procedures. In some embodiments, the posterolateral approach or trajectory can be used in a percutaneous procedure without the need for using a needle stopper. It should be understood that although one needle stopper is shown, there can be more than one needle stopper (e.g., two, three, four, five, etc.) each with the same or varying diameters. In some embodiments, if a plurality of needle stoppers is used, they can be stacked on each other and each one has increasing diameter as the needle tip is approached.

Referring to FIG. 3A-3E, shown therein is an illustration of the extension radiofrequency electrode 145 shown as a coil 147 from a needle tip at the end of the cannula 120. In practice, the length of extension of the coiled radiofrequency electrode 145 will, inter alia, depend on the site in need of ablation. Thus, the electrode is capable of extension or deployment to be tailored to particular treatment needs. For example, the longitudinal axis of the cannula 120 is shown as AA and the RF electrode can be slid out of the needle tip 140 of the cannula as the adjustment member is rotated.

The needle stopper 130 can be transverse to the cannula and radially expand along axis BB in FIG. 3A. In FIG. 3B, the cannula can have a cooling channel 136 extending longitudinally within the cannula such that fluid can be used to cool the RF electrode 145. The cooling channel can run parallel to the RF electrode at all or discrete portions of the cannula. Suitable cooling fluids include water, saline, normal saline, dextrose, and combinations thereof to cool the electrodes. In some embodiments, the cooling channel can also be used to deliver a therapeutic agent.

In some embodiments, insulation material 131 can be disposed between electrodes so that efficient cooling and/or heating can be accomplished. In some embodiments, a second electrode or return electrode 133 can be disposed within the cannula shown in FIG. 3B. This is a bipolar probe where both electrodes are in one cannula and each electrode can receive, conduct and/or discharge RF current. In some embodiments, the insulation material can be disposed between the first and second electrode to further insulate the two electrodes. The insulation can be disposed at discrete positions within the cannula to better assist cooling and/or heating.

Figure 6:
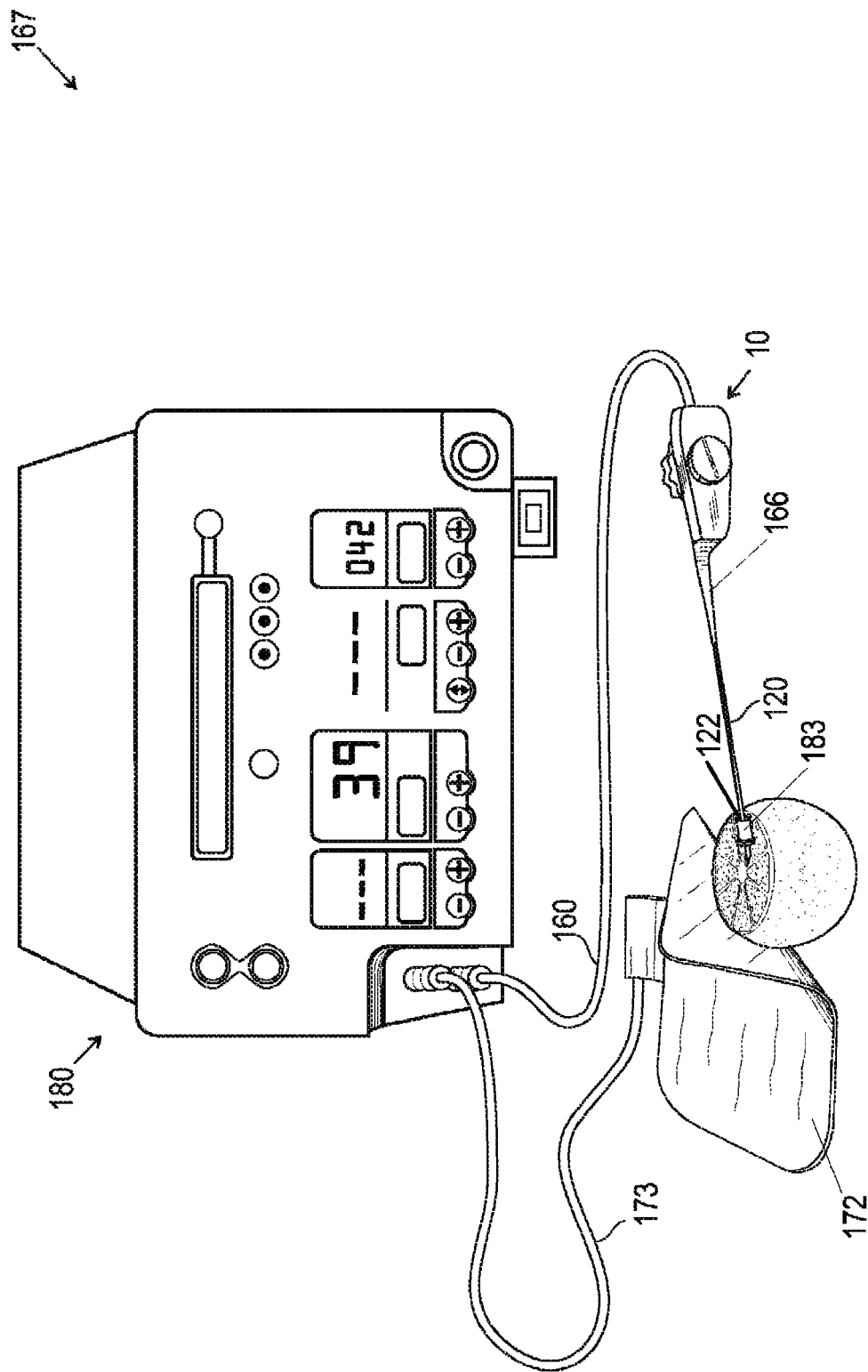
FIG. 6 shows a radiofrequency ablation apparatus and computer control system for the radiofrequency ablation apparatus.

In some embodiments, a return electrode 172 can be outside the cannula, see FIG. 6 at 172 where the second or return electrode is outside of the cannula. This is a monopolar probe. As described above, in some embodiments a return electrode can be inside the cannula, a bipolar probe, see, for example, FIG. 3B, where the second or return electrode is shown inside the cannula at 133. The return electrode or passive electrode of both monopolar and bipolar probes receive, conduct, and/or transmit RF energy but generally does not discharge RF energy to heat tissue. Both monopolar and bipolar probes receive, conduct, and/or transmit RF energy. The return electrode or passive electrode, in some embodiments, does not discharge RF energy to heat tissue.

In some embodiments, an insulation material, or insulator 131 is disposed between the electrodes 145 and 133 of FIG. 3B. Insulators prevent electrical contact between the electrodes and allow better control over heating and/or cooling of tissue. A variety of insulating materials may be used. For example, in some embodiments, insulators such as polyolefins, biaxially-oriented polyethylene terephthalate, silicone, polysulfone, ceramics, composites, or other dielectric materials, can be used as insulators between the electrode configured to receive or conduct radio frequency discharges 145 and the return electrode 172 of FIG. 6.

Referring to FIG. 4A-4D, shown therein is an example of the deployment of a coiled radiofrequency electrode 145 entering a spinal disc nucleus 165 wherein the hosing 100 comprises indicators on the gauge 125, which are calibrated such that each numerical integer increase represents one coil turn extension of the coiled radiofrequency electrode 145. It is understood by persons of skill in the art that in other embodiments the gauge can be calibrated differently. For example, rotating the adjustment member will contact the RF electrode and retract it in the non-deployed or retracted position shown in FIG. 4A.

Figure 4A:
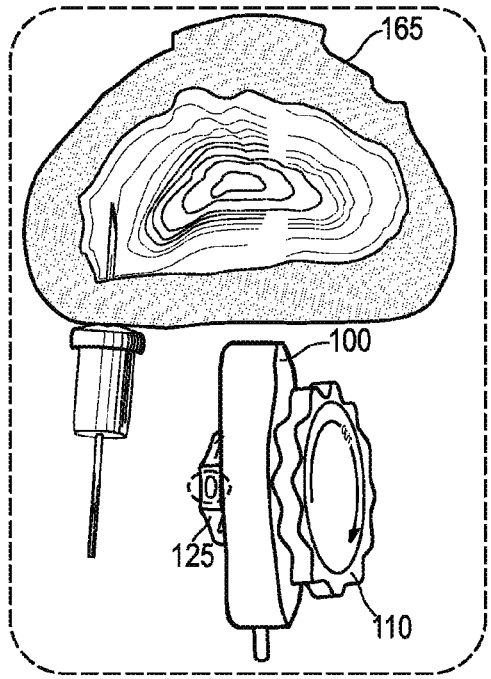
FIGS. 4A, 4B, 4C, and 4D illustrate the extension of a coiled radiofrequency electrode in an intervertebral disc with the adjustment member, gauge, device housing shown.
Figure 4B:
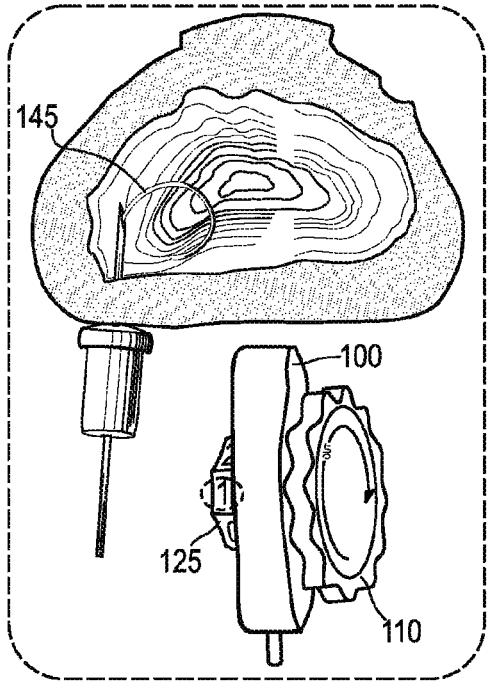
Figure 4C:
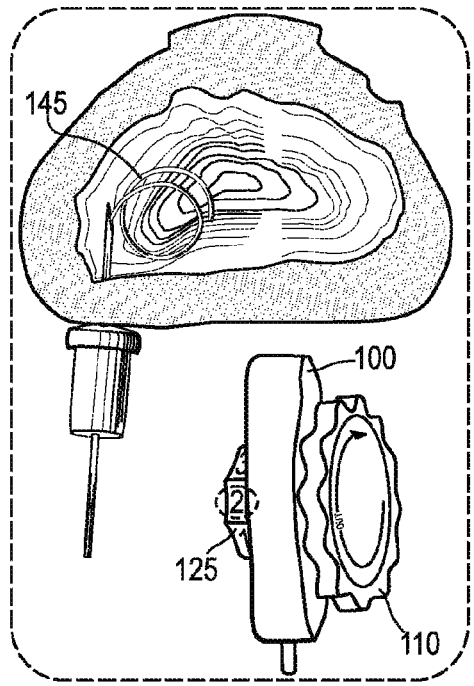

Rotation of the adjustment member 110 to the number one shown on the gauge 125 of FIG. 4B will cause the adjustment member to slidably engage the radiofrequency electrode 145 and cause it to slide out of the cannula to expose one coiled or helical region. The adjustment member 110 can slidably engage the radiofrequency electrode 145 and cause it to slide along the cannula's longitudinal axis. Likewise, rotation of the adjustment member 110 to the number two shown in FIG. 4C on the gauge 125 will cause the adjustment member to slidably engage the radiofrequency electrode 145 and cause it to slide along the longitudinal axis of the cannula and out of it to expose two coiled or helical regions.

Figure 4D:
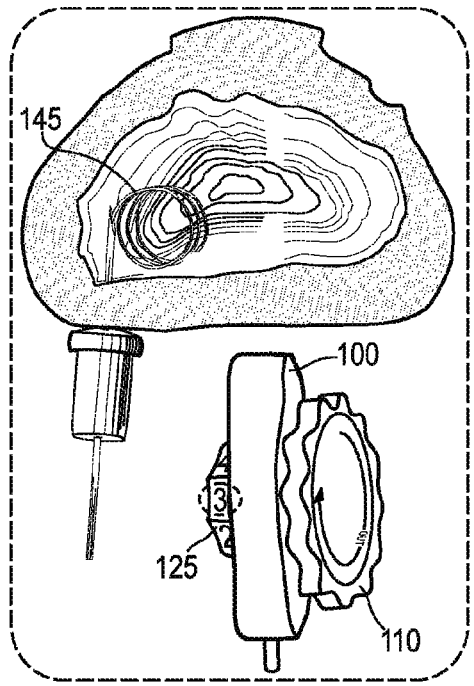

Rotation of the adjustment member 110 to the number three shown on the gauge 125 of FIG. 4D will cause the adjustment member to slidably engage the radiofrequency electrode 145 and cause it to slide along the longitudinal axis of the cannula and out of it to expose three coiled or helical regions. The coil or helical region of the RF electrode in the deployed position allows for increased surface area for target tissue heating. The RF electrode can also heat the tissue in a more controlled manner and cause the desired necrosis of the tissue. The RF electrode can ablate the heat effective zone more evenly and in a controlled manner and the RF electrode can be extended and adjusted so as to focus the RF energy on the complete area and avoid ablating or charring unwanted tissue.

Figure 5:
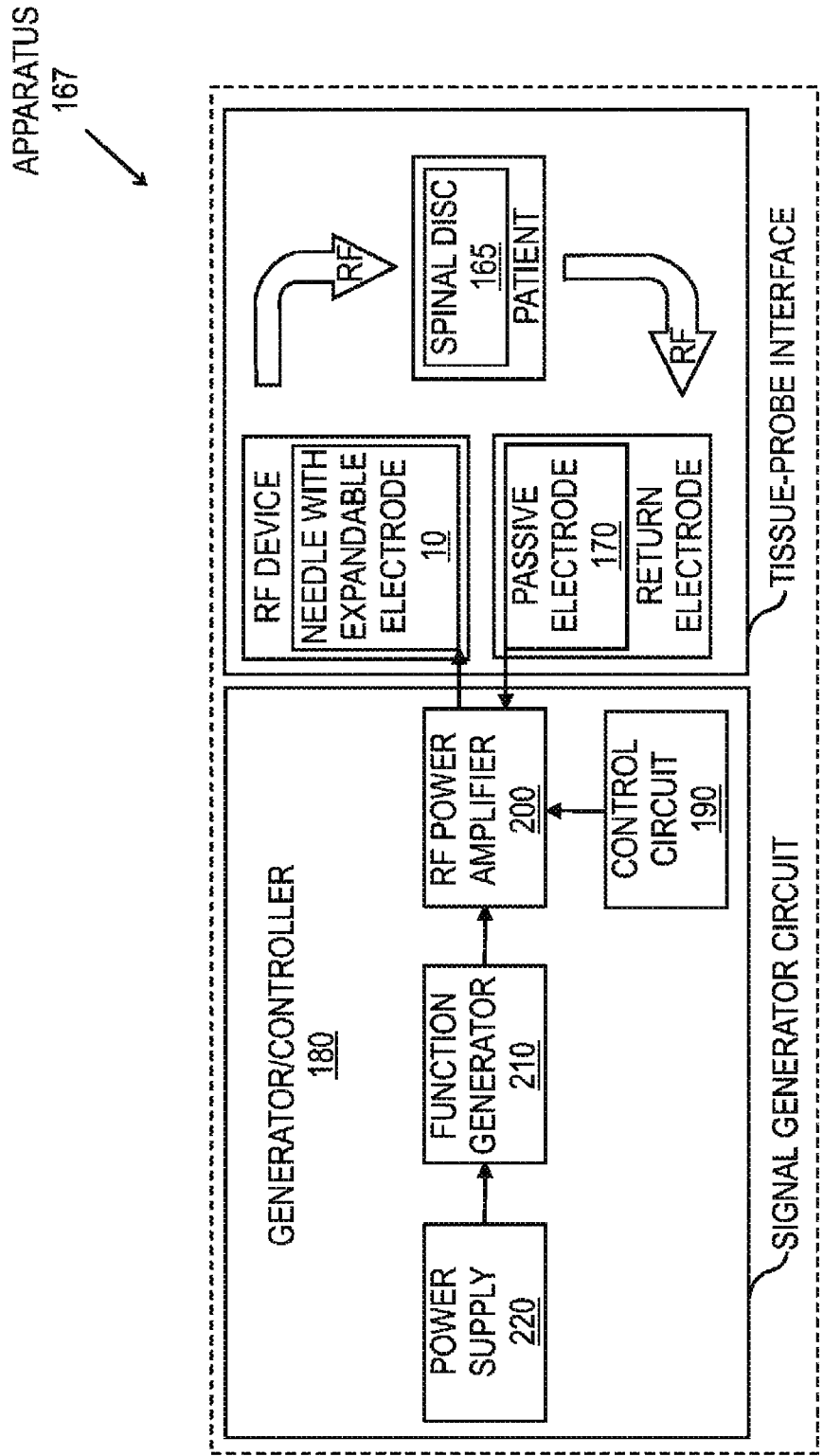
FIG. 5 is a schematic diagram illustrating an embodiment of the radiofrequency ablation apparatus in accordance with teachings disclosed herein.

FIG. 5 illustrates a schematic flow diagram of an apparatus 167 for providing radiofrequency treatment in accordance with some embodiments disclosed herein. FIG. 5 shows the interface between a Generator/Controller and an RF electrode with the expandable electrode 166 for providing radiofrequency treatment to spinal disc 165, and a return electrode 172 and a passive electrode 170. The Generator/Controller 180 comprises a control circuit 190, a power supply 220, a function generator 210, and an RF power amplifier 200. The signal generator circuit allows for RF current to be generated and operated under the generator control 180, which allows a specific setting for RF generation and control of the RF energy generated as well as the on/off or pause control of the RF energy. The apparatus can also measure tissue impedance as the RF ablation device contacts the target tissue site to monitor ablation at the tissue probe interface.

It will be understood that although the RF electrode with the expandable electrode 166 and the passive electrode 170 and return electrode 172 are shown as separate electrodes, they can be in one probe or cannula or they can be in separate probes or cannulas. It will also be understood that the passive electrode or return electrode, in some embodiments, can receive and conduct RF current away from the target tissue site, which can then be used by the control circuit to monitor tissue ablation.

The return electrode, passive electrode and/or RF electrode may be of any designs, sizes or shapes. The return electrode, passive electrode and/or RF electrode can be integral with the cannula or needle or separated from it.

In some embodiments, the return electrode and/or passive electrode can be located inside or outside of disc space. If inside disc space, in this embodiment, the return electrode and/or passive electrode may be inserted into disc space together or independently, at the same side as cannula or needle containing the RF electrode or on the opposite side (of the intradiscal space) of cannula or needle containing the RF electrode.

In some embodiments, the return electrode 172 can receive, conduct and discharge RF energy as the RF electrode. In some embodiments, this is accomplished by a switch member that splits the RF energy or directs the RF energy to the return electrode.

In some embodiments an apparatus for providing radiofrequency treatment comprises a device for providing radiofrequency treatment and an electrical connection assembly configured to electrically couple the radiofrequency electrode to a power source 220 that is part of a generator controller unit 180 that can convert the energy to the appropriate RF frequency, of which further details, in some embodiments, are described in FIG. 5.

FIG. 6 shows an apparatus for providing radiofrequency treatment 167, illustrating the physical units described schematically in FIG. 5. Shown in FIG. 6 are, in accordance with some embodiments, a radiofrequency electrode 166, a generator/controller 180, and a return electrode 172. RF energy is conducted to radiofrequency electrode 166 via connector 160 and RF energy is returned to the return electrode 172 via connector 173. The RF energy can return after contacting the target tissue site.

Figure 7:
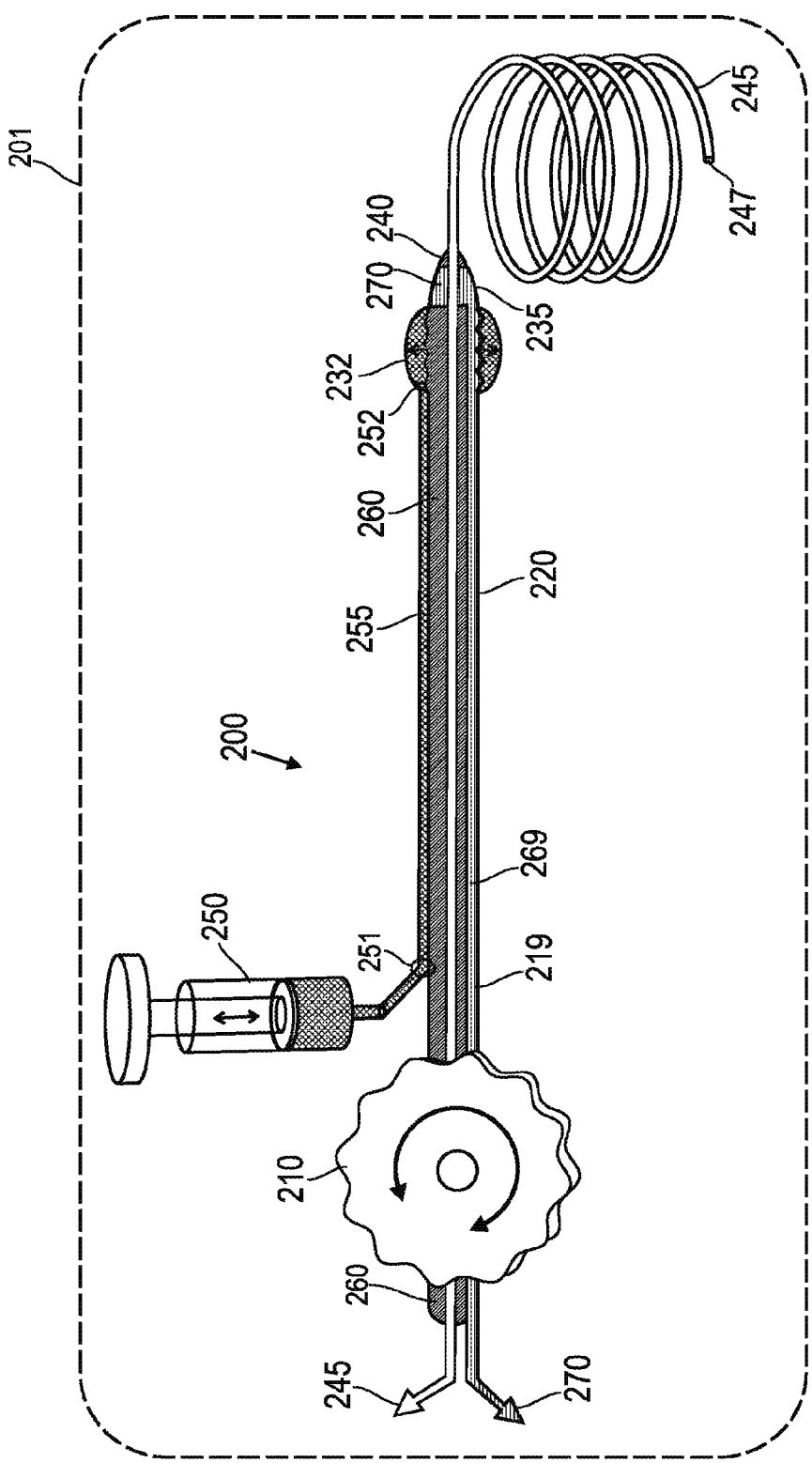
FIG. 7 shows a radiofrequency ablation device that includes an inflatable member for anchoring.

Referring to FIG. 7, shown therein is an example of an embodiment of a RF treatment device 200 for providing radiofrequency (RF) treatment to a target tissue. The RF treatment device 200, in this embodiment comprises an inflatable anchor member shown as an inflatable anchor balloon 232 and generally, the RF treatment de vice 200 comprises a device housing 201, an adjustment member 210, a cannula 220 having a proximal end 219 and a distal end 235 and, a radiofrequency electrode 245 also referred to as a first electrode capable of being in a retracted state and an extended or deployed state wherein the radiofrequency electrode extends from the distal end 235 of the cannula 220 past needle tip 240. In some embodiments, the RF treatment device 200 comprises a device housing 201, an adjustment member 210, a cannula 220, an inflatable balloon 232, a tip 240, a second electrode 270, an insulation material 260, an inflation lumen 255 in fluid communication with the inflator 250 and the inflatable anchor balloon 232. In some embodiments the inflator is a syringe and in some embodiments the inflator is a bulb. The inflator can be a pump, in some embodiments, to pass fluid (e.g., air, liquid, etc.) along the inflation lumen to inflate the anchor balloon. In some embodiments there is a port 251 at the proximal end of the cannula 220 and a port 252 at the distal end of the cannula 220. Port 251 can be used to connect an inflator to the inflation lumen 255. Port 252 can be used to connect the inflation lumen 255 to the inflatable anchor balloon 232.

In some embodiments the inflation lumen 255 can be outside of the cannula 220. In some embodiments the inflation lumen can be within the cannula 220. In some embodiments a cooling channel can extend entirely along the longitudinal axis of the cannula 220 or at one or more discrete regions of the cannula 220 to efficiently cool the RF ablation electrode. In some embodiments, the inflation lumen 255 can also comprise a liquid to cool the RF ablation electrode and also function to inflate the anchor member (e.g., anchor balloon).

The insulation material 260 can also be referred to as an insulator. In some embodiments the second electrode is configured to conduct radiofrequency away from the target tissue site. In some embodiments, the insulation material 260 is disposed about the first electrode and configured to reduce or prevent conduction of radiofrequency current in the cannula 220.

The inflatable anchor balloon 232 can be used for anchoring the cannula tip 240 in a desired position or location on a target tissue. The inflatable anchor balloon 232 can be disposed around a portion of the longitudinal axis of the cannula 220 and when inflated have a larger diameter than the diameter of the cannula 220. When deflated the inflatable anchor balloon 232 can have a diameter close, or approximate, to that of the cannula 220. The inflatable anchor balloon 232 can expand radially when inflated and anchor the device at or near the target tissue site (e.g., bone, soft tissue, blood vessel, muscle, tendon, organ, etc.). In some embodiments, the tip 240 can be pointed to allow for easy pushing through tissues. In some embodiments, the tip 240 can be a needle tip. In some embodiments, the tip 240 be round, blunt, or tapered. In various embodiments, the tip can be smooth for insertion. In some embodiments, the radiofrequency electrode 245 has a blunt tip 247 such that the surgeon or health practitioner can eliminate any difficulty in positioning the electrode tip in the optimal location to get an optimal and consistent clinical result.

Referring to FIG. 8, FIGS. 8A-8J, shown therein are detail views of various embodiments of a RF treatment device for providing radiofrequency (RF) treatment to a target tissue relating to first and second electrode configurations. In these details, in some embodiments, the first electrode 245 and the second electrode are separated in the body of the cannula 280 by an insulation material 260, also referred to herein as an insulator 260. The portion of the cannula 280 depicted in FIG. 8 has a proximal end 236 and a distal end 235. The detail views shown in FIGS. 8A-8J are various embodiments that can be included in, for example, the devices depicted in FIG. 1A, FIG. 7, and other such radiofrequency (RF) treatment devices understood by persons of skill in the art.

Figure 8A:
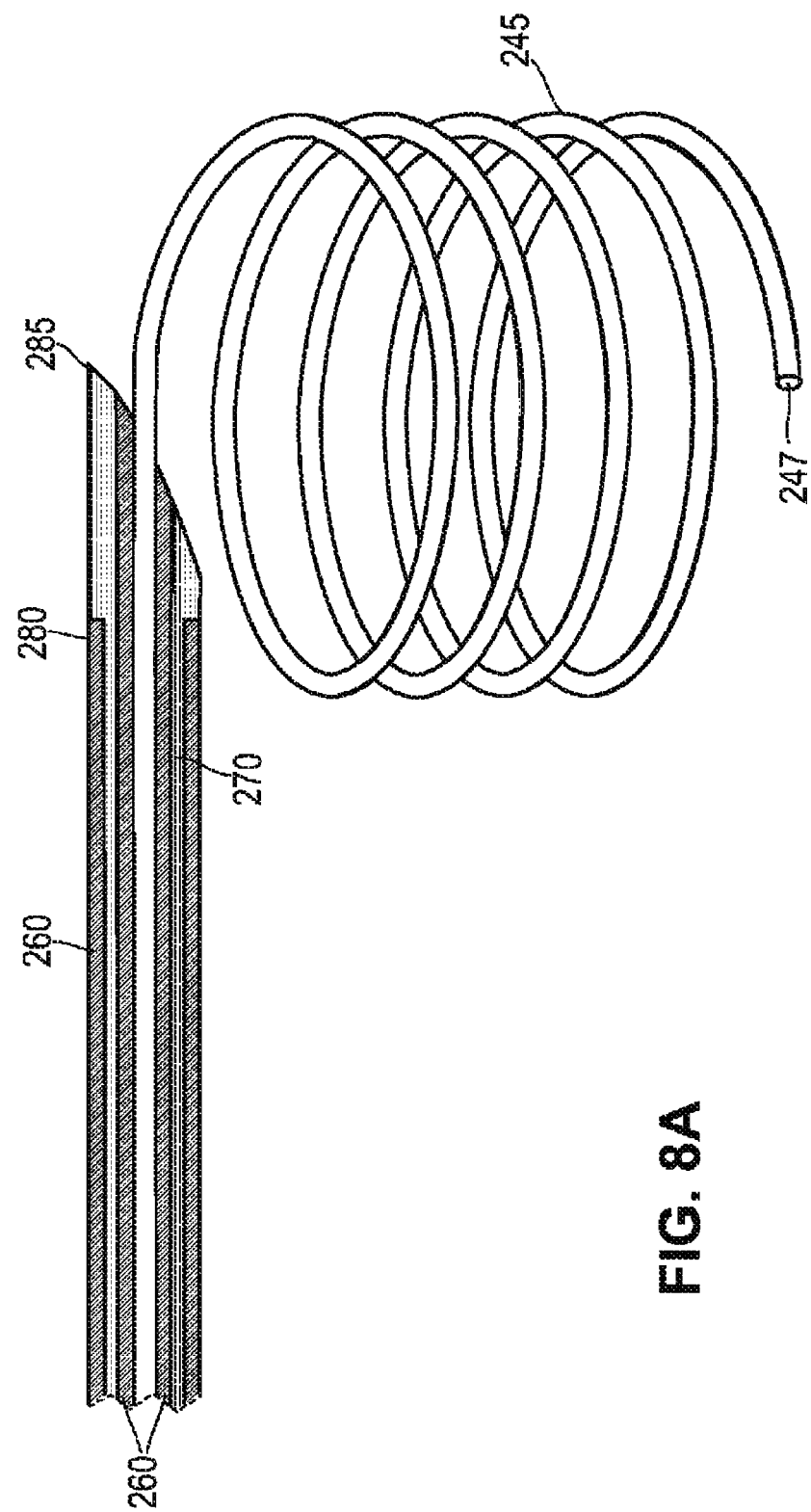
FIGS. 8A, 8B, 8C, 8D, 8E, 8F, 8G, 8H, 8I, and 8J, illustrate various embodiments with different first and second electrode configurations.
Figure 8B:
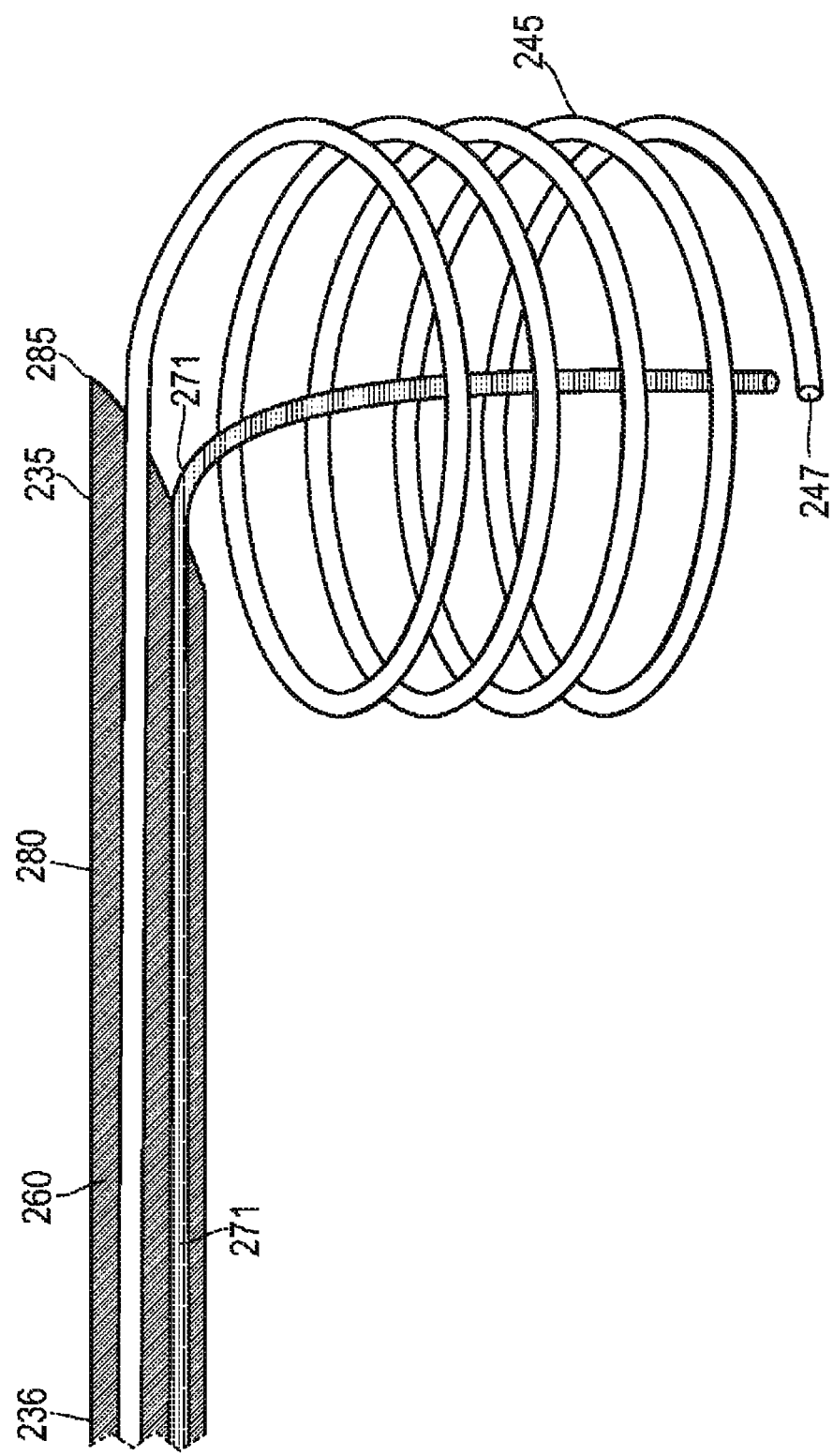

In embodiments where a first electrode 245 and/or a second electrode, such as the second electrode 271 of FIG. 8B, can be extended from the body of the cannula 280, the first electrode 245 and/or the second electrode 271 can be engaged by an adjustment member such as the adjustment member 110 depicted in FIG. 1 or the adjustment member 210 depicted in FIG. 7. In some embodiments, the rotation of an adjustment member 110 of FIG. 1 or adjustment member 210 of FIG. 7 will cause the adjustment member to slidably engage the first electrode 245 and/or the second electrode 269 and cause it to slide along the longitudinal axis of the access cannula and out of it to expose various amounts of extended electrode. Wherein the RF electrode, first electrode 245, is coiled or in a helical arrangement when extended in deployed positions, this allow for increased surface area for target tissue heating. In bipolar configurations, both the first electrode and the second electrode in embodiments wherein these electrodes are extended from the cannula 280, both the first and second electrode can be in extended coiled deployment positions to achieve increased surface area coverage in target tissue heating.

In some embodiments, as shown in FIG. 8A, there is a cannula 280, a radiofrequency electrode 245, also referred to as a first electrode, in an extended coiled state, a second electrode 270, in some embodiments referred to as a return electrode, and an insulation material 260, wherein the second electrode 280 is disposed in such a way as to surround the radiofrequency electrode 245 within the body of the cannula 280. In some embodiments, the second electrode as shown in FIG. 8A has a concentric tubing configuration and surrounds the first electrode 245 within the cannula 280. In some embodiments the tip 285 is sharp. In some embodiments the tip 285 is a needle tip. In some embodiments the tip 247 of the radiofrequency electrode 245 can be a blunt tip such that the surgeon or health practitioner can eliminate any difficulty in positioning the electrode tip in the optimal location to get an optimal and consistent clinical result.

In some embodiments, as shown in FIG. 8B, the second electrode 271 is flexible and extendable beyond the tip 285 of the distal end 235 of the cannula 280. In some embodiments the second electrode comprises a flexible material such as nitinol wire. In some embodiments there is no physical contact between the extended regions of the first electrode 245 and the second electrode 271. In the embodiment shown, the second electrode 271 is flexible and extendable beyond the tip 285 of the distal end 235 of the cannula 280, where it has a bend portion, but is not coiled. The second electrode 271 in this embodiment is disposed substantially in the center of the coiled region of the first electrode 245 and adjacent and just above the tip 247. In some embodiments, the second electrode can conduct RF energy away from the target tissue site.

Figure 8C:
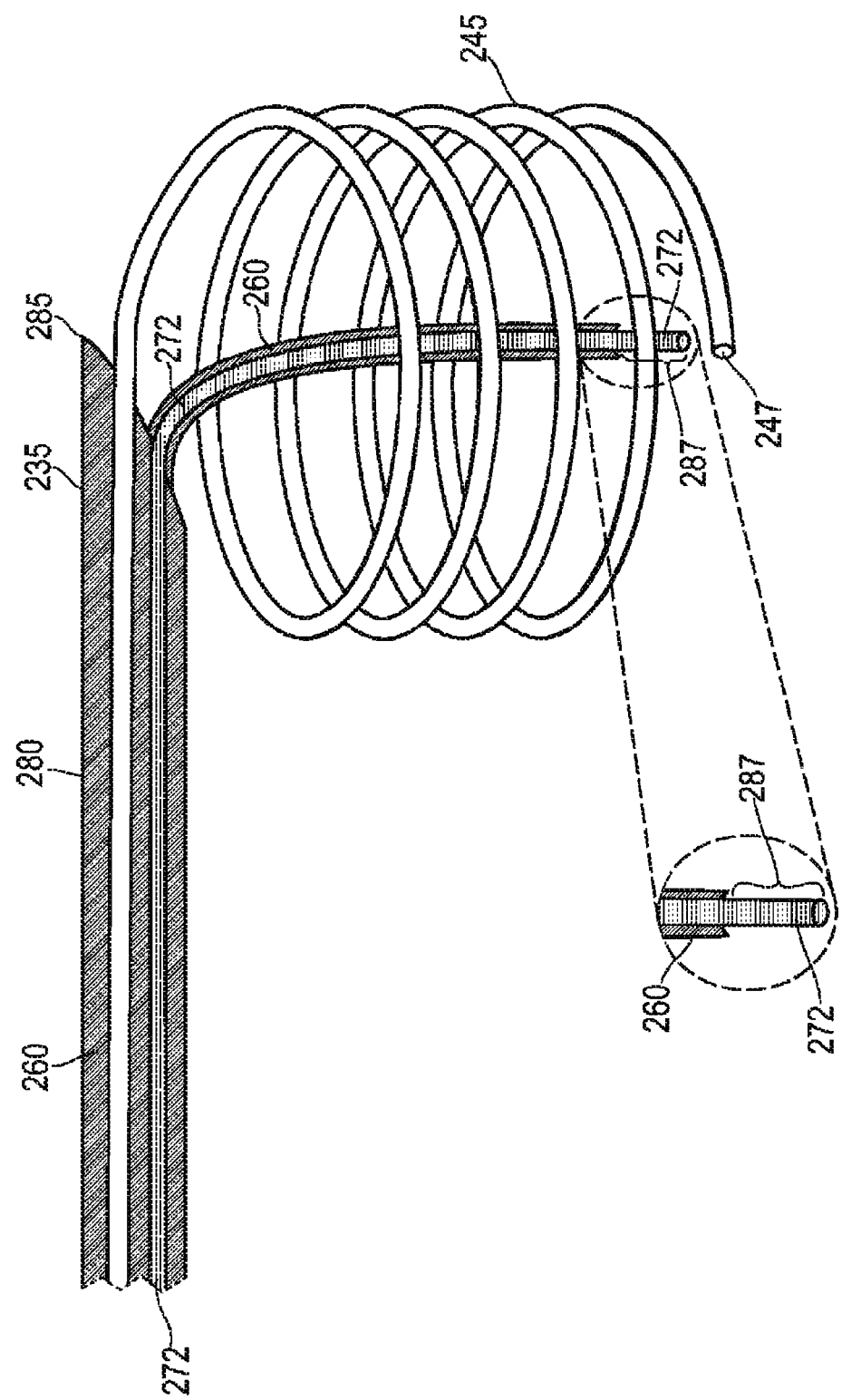

In some embodiments, as shown in FIG. 8C, the second electrode 272 is extendible from the cannula 280 at the distal end 235 and flexible and its surface is coated with insulation 260 except for a region 287 near the distal end of the second electrode 272. In the embodiment shown, the second electrode 272 is flexible and extendable beyond the tip 285 of the distal end 235 of the cannula 280, where it has a bend portion, but is not coiled. The second electrode 272 in this embodiment is disposed substantially in the center of the coiled region of the first electrode 245 and adjacent and just above the tip 247. In the embodiment shown, there is no insulation at the distal end of the second electrode by region 287. This allows for better conduction of RF energy away from the target tissue site. The insulation 260 prevents or reduces the scatter of RF energy and allows for better control of the RF energy.

Figure 8D:
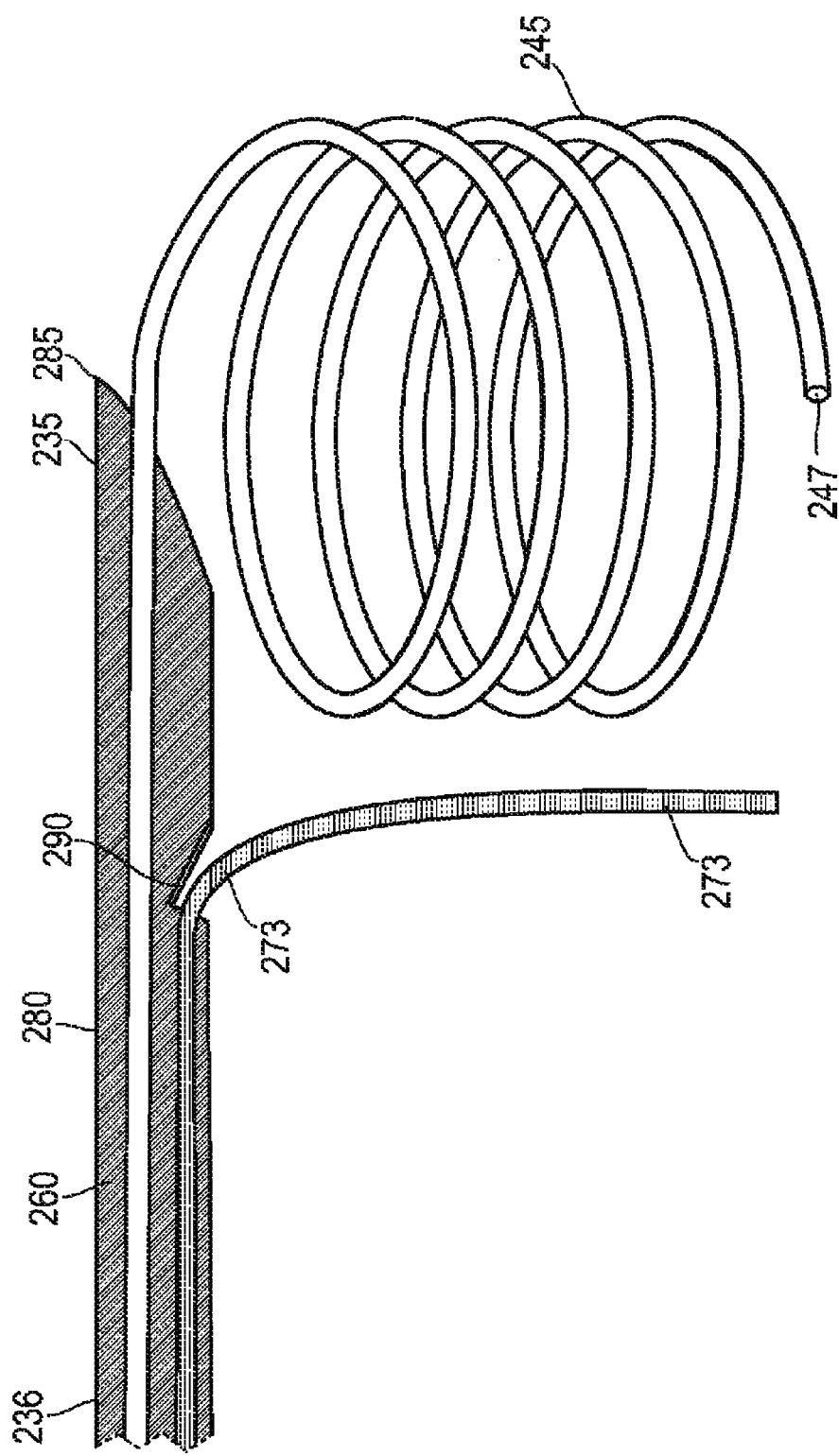

In some embodiments, as shown in FIG. 8D, the second electrode 273 is extendible from the cannula 280 and flexible, the second electrode can be extended from the cannula 280 at various distances from the cannula tip 285 by being diverted by a deflector 290 in the wall of the cannula 280. A person of skill in the art can choose various distance relationships between the second electrode 273 and the first electrode 245 in accordance with the needs of the procedure. In some embodiments, the surface of the second electrode 273 can be coated with insulator material. The first and/or second electrode can be engaged by the adjustment member 110 of FIG. 1A so that each electrode can be selectively deployed out of the cannula. In some embodiments, there can be one adjustment member that allows adjustment of both electrodes. In some embodiments, there are two adjustment members that allow adjustment of each electrode independently. The deflector 290 shown as an angled surface can be movable or immovable prong, ridge, clip, spring, friction fitting, or the like and function as a guide to guide the second electrode tip out of the cannula. In some embodiments, the deflector 290 can close on the second electrode and prevent bodily fluid from backing up into the device. In some embodiments, the deflector 290 can be engaged by the adjustment member so that it can open to let a portion of the second electrode pass out of it. In some embodiments, it can close to prevent deployment of the second electrode.

Figure 8E:
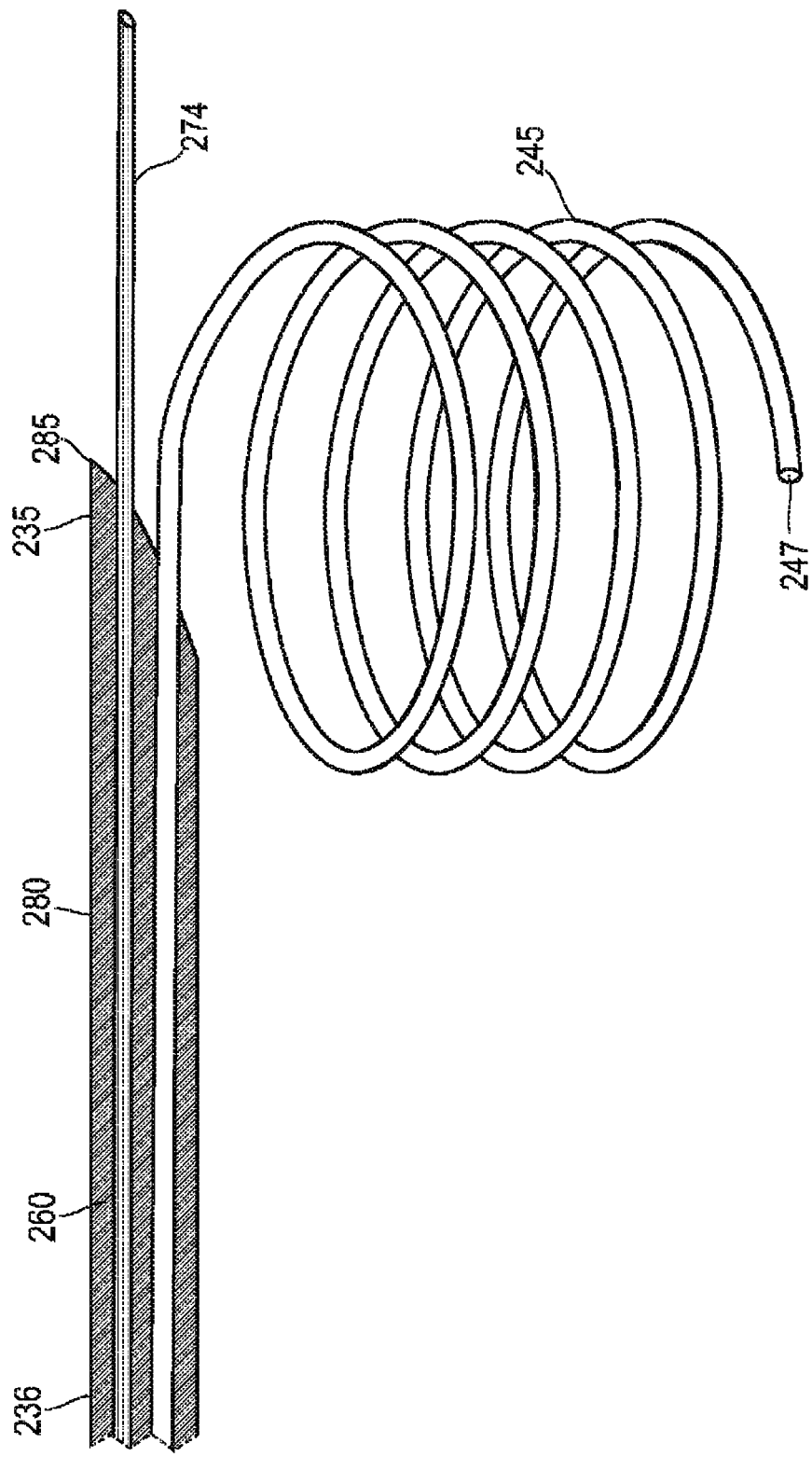

In some embodiments, as shown in FIG. 8E, the second electrode 274 can be rigid when extended from the tip 285 of the cannula 280 and separate from the extended first electrode 245 that can have a coiled shape. In some embodiments, the second electrode 274 can be insulated in the region extended from the cannula tip 285. In some embodiments, the rigid extended second electrode 274 can be separated from the first electrode 245 by an insulator 260 within the cannula.

In the embodiment shown, the second electrode 274 is rigid and extendable beyond the tip 285 of the distal end 235 of the cannula 280, where it extends longitudinal in a planar direction without any bend portion, but is not coiled. In the embodiment shown, the second electrode is disposed and deployed above the first electrode and extends beyond the tip 247 of the first electrode. The insulation 260 prevents or reduces the scatter of RF energy and allows for better control of the RF energy. In the embodiment shown, the insulation is disposed above the electrode at discrete regions of the cannula and is designed to control heating of the electrode.

Figure 8F:
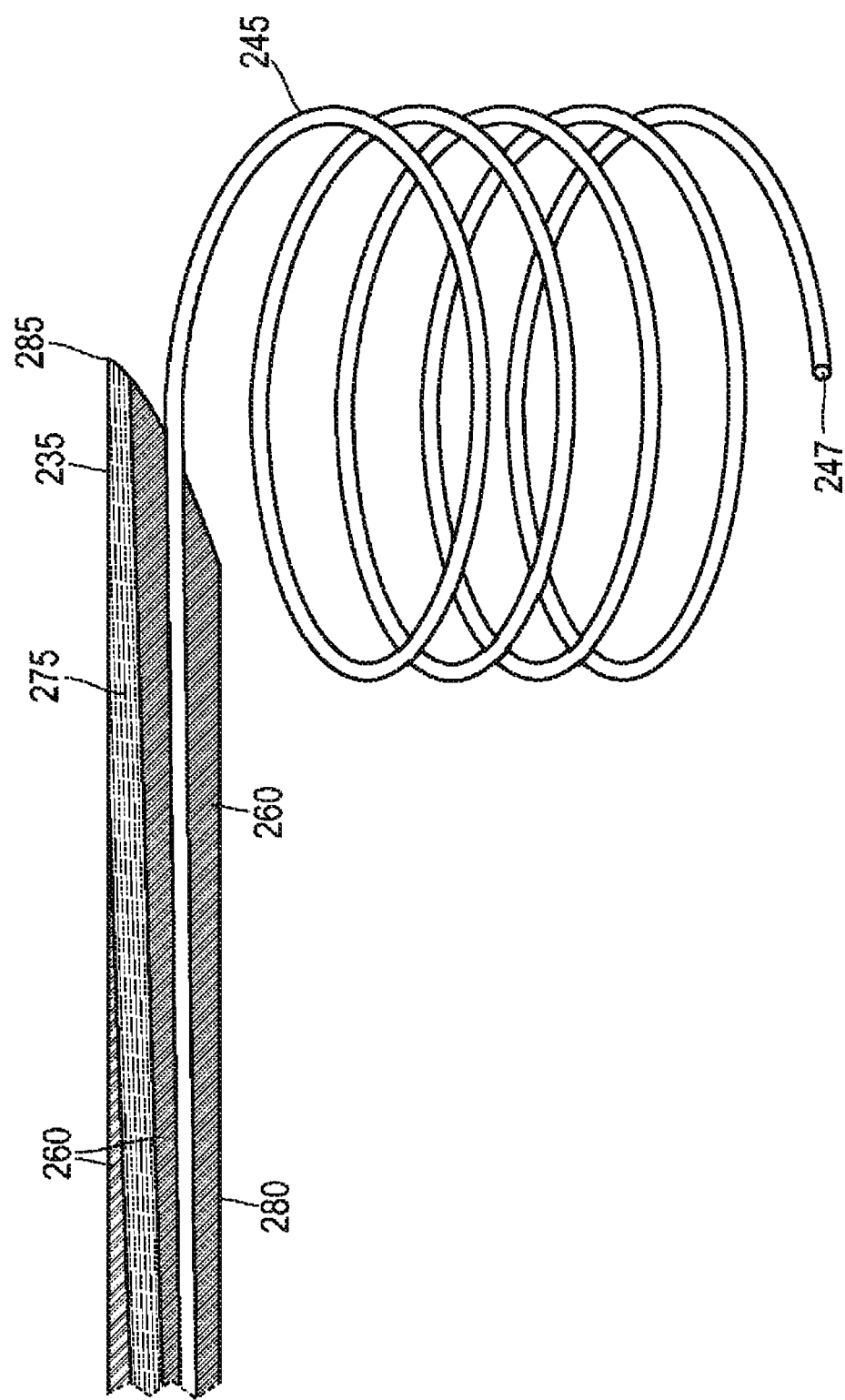

In some embodiments, as shown in FIG. 8F, the second electrode 275 is stationary and disposed within the cannula 280 and is uninsulated, or uncoated, with insulator material 260 in a region near the cannula tip 285 at the distal end 235 of the cannula 280 and coated with insulator material 260 at the proximal end of the cannula 280. In the embodiment shown, there is no insulation at the distal end of the second electrode by region. This allows for better conduction of RF energy away from the target tissue site. The insulation 260 prevents or reduces the scatter of RF energy and allows for better control of the RF energy.

Figure 8G:
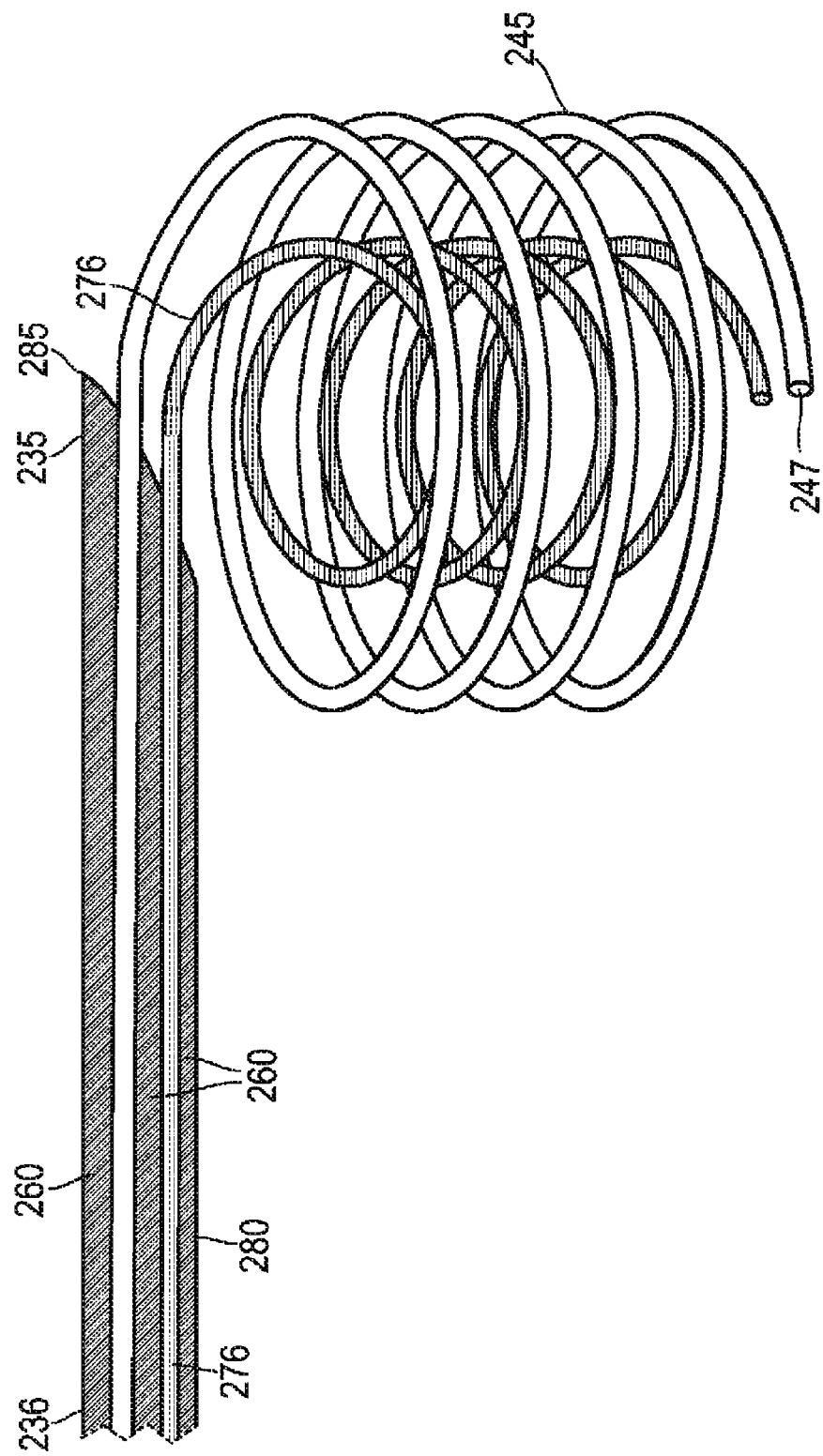

In some embodiments, as shown in FIG. 8G, the second electrode 276 when extended from the cannula tip 285 is configured to become a concentric coil disposed within the coiled first electrode 245 but not making contact with the first electrode 245. The second electrode 276 in this embodiment is disposed substantially in the center of the coiled region of the first electrode 245 and adjacent and just above the tip 247. In some embodiments, the second electrode can conduct RF energy away from the target tissue site and there is controlled heating and cooling of the electrode and, therefore, target tissue site. It will be understood that both electrodes can have insulation material coated thereon at discrete regions of the electrodes.

Figure 8H:
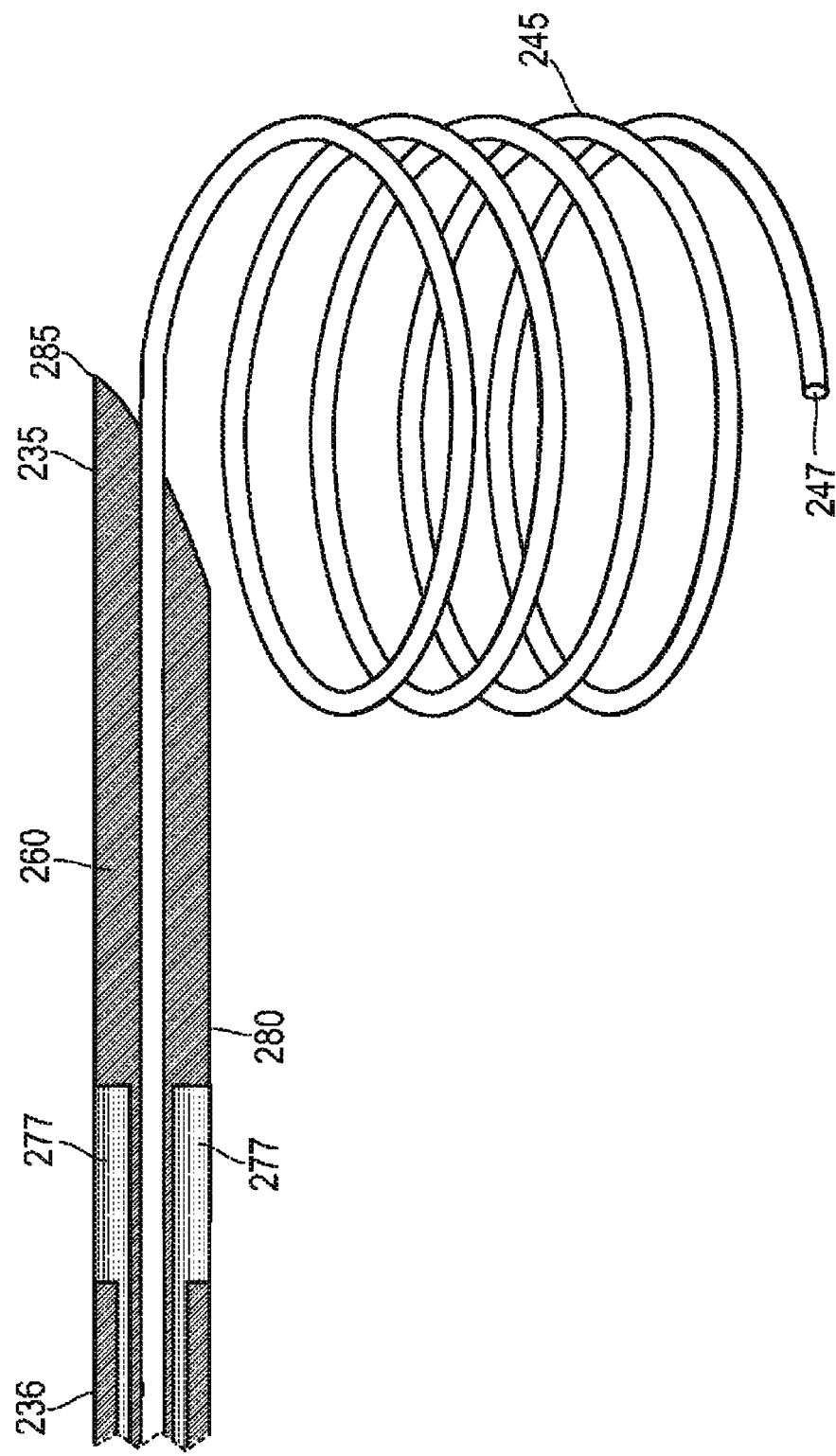

In some embodiments, as shown in FIG. 8H, the second electrode 277 is disposed within the cannula 280 away from the region of the cannula tip 285, on the proximal end 236, and separated from the first electrode by an insulator 260. In some embodiments, the second electrode 277 is disposed such that it contacts and/or forms the wall of the catheter 280 for a region at the proximal end 236 of the portion of the cannula shown in FIG. 8H.

Figure 8I:
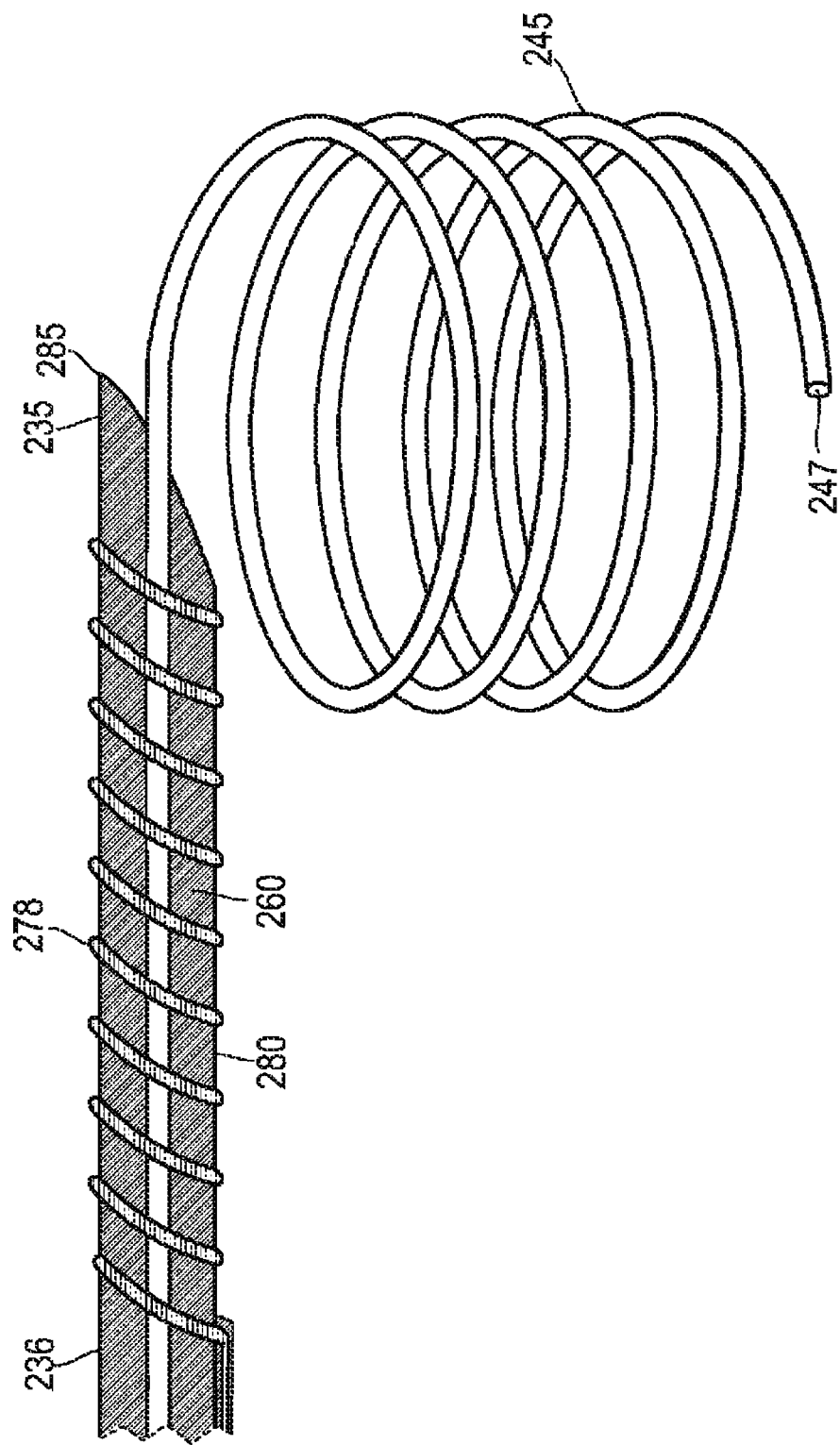

In some embodiments, as shown in FIG. 8I, the second electrode 278, takes on a coiled configuration spiraling around discrete regions of the outside of the cannula 280 and separated from the first electrode 245 by an insulator 260.

Figure 8J:
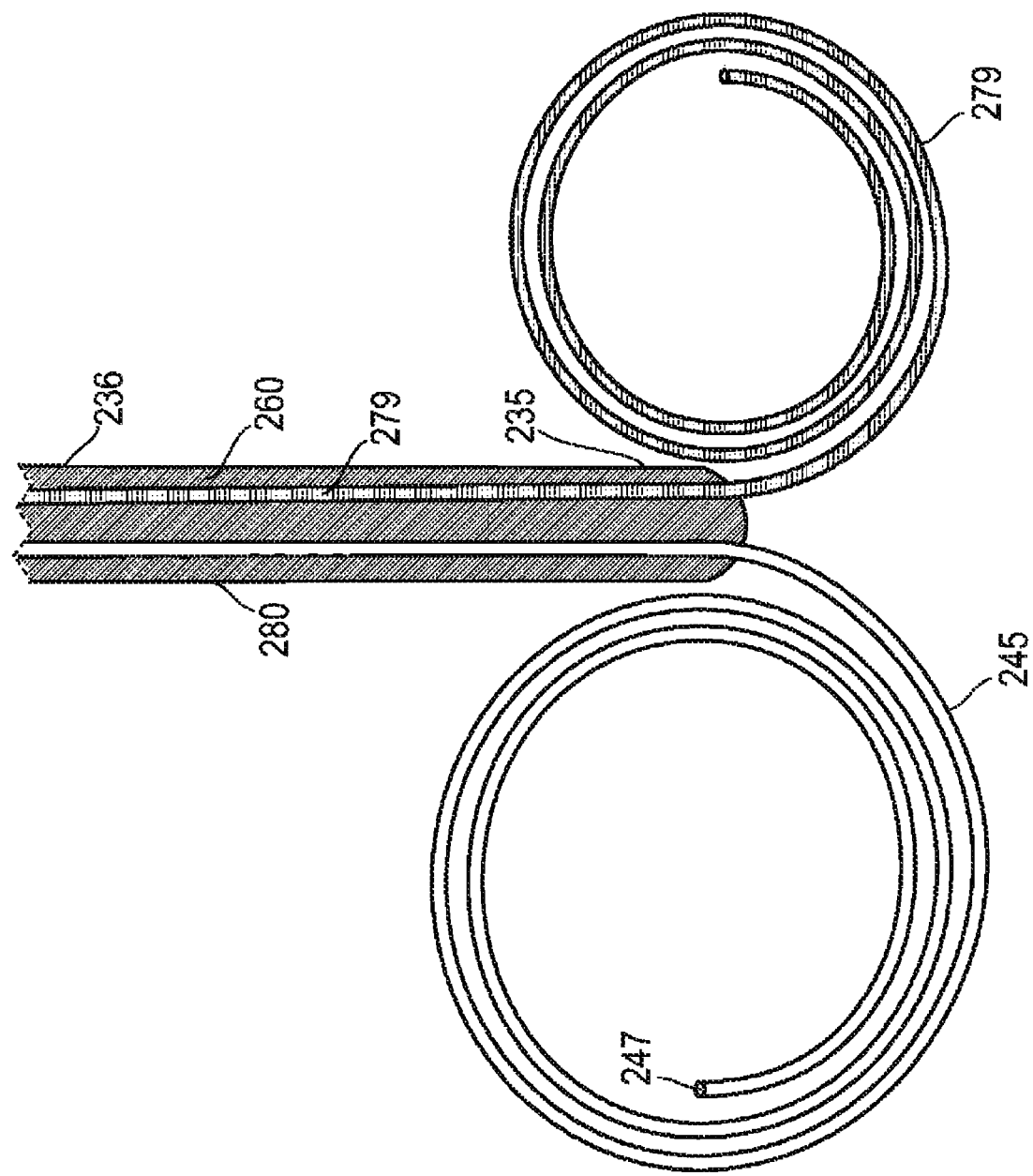

In some embodiments, as shown in FIG. 8J, the second electrode 279 takes on a coiled configuration when extended from the cannula 280 at the distal end of the portion of the cannula shown in FIG. 8J. In some embodiments, the coiled confirmation of the second electrode 279 is a smaller, or tighter coil, than the first electrode 245 coil.

In some embodiments, a method for providing radiofrequency treatment to an intervertebral disc of a patient is provided wherein an inflatable anchor balloon anchors the tip of a cannula at a desired location for treatment. The method for comprises providing a device comprising an cannula having a proximal end and a distal end and a longitudinal axis therebetween, the distal end comprising a needle tip; a radiofrequency electrode for heating a target tissue site, the radiofrequency electrode comprising a distal end and a proximal end, the distal end configured to be placed into the cannula and configured to become a coiled region when urged out of the cannula, the proximal end configured to contact or be coupled to a radiofrequency source; an inflatable anchor balloon disposed around a portion of the longitudinal axis of the cannula and when inflated having a larger diameter than the diameter of the cannula and being configured to anchor the cannula tip at a desired location and/or depth; an inflator, and an inflation lumen defined in fluid communication with the inflator and the inflatable anchor balloon; inserting the cannula up to a desired location and/or depth of the annulus fibrosus; inflating the inflatable anchor balloon to anchor the cannula tip at the desired location and/or depth; extending the radiofrequency electrode to a desired region of tissue for treatment; and activating the radiofrequency electrode to apply radiofrequency energy for a sufficient time to provide radiofrequency treatment to the intervertebral disc. In some embodiments, the method comprises the steps of retracting the radiofrequency electrode, deflating the inflatable anchor balloon, and retracting the cannula from the patient. In some embodiments, the inflator is a syringe or a bulb.

In some embodiments, the apparatus for providing radiofrequency treatment 167 has the proximal end of the radiofrequency electrode 166 engaged with an adjustment member to selectively extend, expand, or retract the coiled region from the cannula at or near the target tissue site. In some embodiments, the adjustment member is a rotary dial, or wheel, that can be turned in a clockwise or counterclockwise direction and is described above as an adjustment member 110 of FIGS. 1A-1E.

In some embodiments, the length of the electrodes that can be introduced can be, for example, from about 10 mm to about 150 mm or from about 50 to about 150 mm in length, for example, about 20 mm to about 100 mm or about 65 mm to about 100 mm. Other lengths can be used that are longer or shorter.

In some embodiments, the radiofrequency generator can be operated within the frequency range of 0.1-100 MHz or 5-50 MHz or 1-50 MHz, at generally a net input power of 50-200 W or 1-200 W or 1-100 W for a set treatment time sufficient to ablate the region. The RF ablation period can be from 30 seconds to 60 minutes or from 3 minutes to 30 minutes to sufficiently ablate the target tissue site. Visualization devices such as fluoroscopy to determine if the region of interest has been sufficiently ablated can be used. In some embodiments, the frequency of the energy is in the range of from about 10 to about 40 MHz. In some embodiments, the frequency range is about 15 to about 30 MHz. In some embodiments, the frequency of the energy can be in the range of about 30 to about 40 MHz, in some embodiments, the frequency of the energy can be between about 100 kHz and 1 MHz, between 400 kHz and 600 kHz, between 300 kHz and 500 kHz, between 350 kHz and 600 kHz, between 450 kHz and 600 kHz, and in overlapping ranges thereof, or any frequency within the recited ranges.

In some embodiments, a bipolar probe can be used for the ablation wherein a second electrode, or return electrode 172, is included with the RF electrode 166 or apparatus 167 such that the circuit is completed without the need for an additional circuit to ground the system. The return electrode 172 can be closely integrated with radiofrequency electrode 166 or separated from it. In some embodiments when treating an intervertebral disc the return electrode 172 can be located inside the disc space. In some embodiments when treating an intervertebral disc the return electrode can be located outside the disc space.

The RF electrode and the return electrode can, in various embodiments, be spaced from each other by about 1 mm, 2 mm, 3 mm, 4 mm, 5 mm, 6 mm, 7 mm, 8 mm, 9 mm or 1 cm. In various embodiments, in addition to coiled electrodes, electrodes comprise cylindrical electrodes, tip electrodes, plate electrodes, curved electrodes, circular electrodes, or other shapes can be used. In some embodiments, a plurality of RF electrodes, return electrodes and/or passive electrodes can be used in an electrode array for RF ablation.

Where a bipolar configuration between the radiofrequency electrode 166 and the return electrode 172 is not established, the radiofrequency electrode should be grounded, in some embodiments with the body of the patient undergoing treatment.

The RF generator 180 may output a modulating signal or a constant waveform as the excitation signal. After RF treatment the RF electrode 166 is removed.

The sizes of the tips of the RF electrode 166 can vary in size depending on the application and is understood by persons of skill in the art. In some embodiments, the cannula or needle for RF ablation can be insulated where, in some embodiments, the diameter of the insulation is less than 1.5 mm, in some embodiments less than 1.0 mm. In some embodiments from about 1.0 mm to about 1.5 mm.

In some embodiments, a temperature sensor 122 can be used for measuring the temperature of the tissue or other material at the RF electrode. In some embodiments, the temperature sensor can be a thermocouple. In some embodiments, a thermistor, a thermometer, an optical fluorescent sensor, or other means of sensing temperature can be used.

In some embodiments, two or more temperature sensors can be used. The temperature sensor or thermocouple can be located at or near the needle tip to measure and monitor tissue temperature. The temperature can be constantly monitored and displayed on the generator/controller 180. The temperature sensor can be located or positioned in a similar manner as described above for return electrode. The read-out temperature can be used to properly control the RF heating of tissues. It can be an open-loop or closed-controlled heating depending on capability of the generator/controller.

In some embodiments, the radiofrequency electrode 166 can be operatively connected to semi-steerable or navigational sources for easier guidance into tissues. In various embodiments, the navigational sources can be coupled with a pre-procedure such as for example, CT, MRI, PET scan, etc. so that the target nerve or soft tissue to be ablated can be identified and accurately located during the procedure.

In various embodiments, at a proximal end, the RF electrode 166 can be operatively connected to a vacuum (not shown) for providing suction to an ablated nerve and/or tissue. The vacuum may be used to transmit a vacuum from a vacuum source (not shown) to a receiving aperture (not shown) connected to RF electrode. Any suitable aspirator, cylindrical or otherwise, or other mechanism that creates vacuum upon the movement of an actuating member thereof, may be utilized as a vacuum source.

In some embodiments, the device causes a temperature of between about 40° C. to about 55° C. at or near the radiofrequency electrode. In some embodiments, the device causes a temperature greater than 55° C. at or near the radiofrequency electrode. In some embodiments, the device causes a temperature greater than 55° C. at or near the radiofrequency electrode. In some embodiments, the device causes a temperature greater than 70° C. at or near the radiofrequency electrode. In some embodiments, the device causes a temperature between about 70° C. and about 90° C. at or near the radiofrequency electrode.

In some embodiments, useful monitoring devices comprise sensors that may receive and record data relating to temperature, light, density, impedance, and position of a radiofrequency ablation electrode in the form of current, radiowaves, microwaves, spectroscopy, and the like. In some embodiments, sensors comprising a battery, an electrode, a recharger, a transmitter, a receiver, a transceiver, a sensor, a recorder, a capacitor, a transformer, a system control unit, a programmer, an address/positioning unit, a temperature sensor, a temperature adjuster, a thermogenerator, a thermoelectric generator, a pressure sensor, a pressure adjuster, a mechanical power generator, a photo/light generator, an ultraviolet light generator, an infrared generator, an optical stimulator, a laser, a radiofrequency generator, a magnetic field generator, a mechanical vibration generator, an ultrasonic wave generator, an electrical field generator, a radiation generator or a fuel cell can be used.

In various embodiments disclosed herein, the device and apparatus for providing radiofrequency treatment can be coupled to an imaging modality such as ultrasound, CT, fluoroscopy, MRI, overhead 3D stereotactic system (via pre-procedure MRI and/or CT) allowing the user to visualize or otherwise identify the area covered by the unspecific or tissue/cell-specific ablation.

For example, imaging devices useful in coupling with the ablation device described herein comprise without limitation Magnetic Resonance Imaging (MRI), functional Magnetic Resonance Imaging (fMRI), Magnetic Resonance Spectroscopy (MRS), diffusion MRI (DWI), diffusion tensor MRI (DTI), electroencephalography (EEG), magnetoencephalography (MEG), nuclear neuroimaging, positron emission tomography (PET), single photon emission computed tomography (SPECT), Ictal-Interictal SPECT Analysis by Statistical Parametric Mapping (ISAS), Computed Tomography (CT), x-ray, fluoroscopy, angiography, ultrasonography, transcranial magnetic stimulation (TMS), transcranial direct current stimulation (tDCS), transcranial electrical stimulation (TES), motor evoked potential (MEP), somatosensory evoked potential (SSEP), phase reversal of somatosensory evoked potential, evoked potential, electrocorticography (ECoG), direct cortical electrical stimulation (DCES), microelectrode recording (MER) or local field potential recording (LFP).

In some embodiments, a lubricant is provided to assist in the insertion of needle tip 140 of FIG. 1A within the nerve and/or soft tissue. In some embodiments, the lubricant can be, without limitation, polyethylene glycol (PEG), hyaluronic acid, hyaluronan, lubricin, polyethylene glycol, poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) and any combinations thereof.

In some embodiments, in order to control more accurately the temperature and pressure, the monitoring device can be comprised of a thermocouple or a thermistor, a pressure sensor 183 and a position sensor all in one control system or separate control systems. In some embodiments, the various sensors may be disposed on a component of the ablation device and/or can be positioned to contact the body tissue targeted for ablation. In some embodiments, the apparatus or device disclosed herein comprises a thermocouple, or other temperature sensor, located near the needle tip 140.

In some embodiments, the device is coupled to software that enables the real time or retrospective review of the data coming from different navigation, monitoring and diagnostic tools used during the ablation procedure. For example, in various embodiments, the monitoring device can take many different forms. In some implementations, the monitoring device is a dedicated electrical circuit employing various sensors, logic elements, and adjustment members. In other implementations, the monitoring device is a computer-based system that includes a programmable element, such as a microcontroller or microprocessor, which can execute program instructions stored in a corresponding memory or memories. Such a computer-based system can take many forms, may include many input and output devices, and may be integrated with other system functions, such as the monitoring device, imaging device, a computer network, and other devices that are typically employed during an ablation procedure. For example, a single computer-based system may include a processor that executes instructions to provide the function of the monitoring device; display imaging information associated with an ablation procedure (e.g., from an imaging device); display pressure, temperature, time information (e.g., elapsed time since a given phase of treatment was started) and probe position; and serve as an overall interface for the ablating device. In general, various types of monitoring devices are possible and contemplated, and any suitable monitoring device can be employed.

Suitable material for the cannula 120 and/or device housing 100 can be, for example, polyurethane, polyurea, polyether(amide), PEBA, thermoplastic elastomeric olefin, copolyester, and styrenic thermoplastic elastomer, nylons, polyimides, other thermoplastics, and the like. Persons of skill in the art would know other materials that can be used. In some embodiments, any insulator, non-conducting, material that has appropriate mechanical properties can be used.

In various embodiments the RF electrode 166, can be formed of Nitinol (e.g. NDC-Nitinol Devices & Components, Fremont, Calif., USA). Nitinol has an electrical conductivity similar to that of stainless steel, is MR compatible, biocompatible, and has very high corrosion resistance. In embodiments where Nitinol is used, to avoid stress-strain effects, the coiled portion should preferably not be stored in the retracted state. In some embodiments, other memory metals can be used, such as a memory metal, such as nickel titanium.

Preparation and use of flexible RF electrodes that can be coiled, in accordance with some embodiments disclosed herein, are known in the art. See, for example, U.S. Pat. No. 8,073,551 to McCann et al. and U.S. Patent Publication No. 20140031715 to SHERAR; Michael David; et al. (filed as U.S. application Ser. No. 13/954,647). U.S. Pat. No. 8,073,551 to McCann et al. and U.S. Patent Publication No. 20140031715 to SHERAR; Michael David; et al. (filed as U.S. application Ser. No. 13/954,647) are both hereby incorporated by reference.

In various embodiments, the RF electrode may include radiographic markers to help indicate position on imaging procedures (e.g., CT scan, X-ray, fluoroscopy, PET scan, etc.). These may be disposed on or a portion of the RF electrode and include, but are not limited to, barium, calcium phosphate, and/or metal beads.

In some embodiments, RF electrode can also have blunt tips. As a result, the surgeon or health practitioner can eliminate any difficulty in positioning the probe tips in the optimal location to get an optimal and consistent clinical result.

In certain embodiments, RF electrode can be provided with a tube or small channel (not shown) configured to deliver at the location of the severed nerve and/or soft tissue cement or polymer which can provide a physical barrier to prevent the temporary or permanent re-growth of nerve and/or soft tissue so that the pain symptoms do not return. This channel can be adjacent to the electrodes and can run parallel to the electrodes such that the device can ablate and deliver a therapeutic material or barrier (e.g., polymer, cement, gel, etc.) to the area after ablating it.

Methods for Ablation

The present disclosure also provides methods of applying radiofrequency energy to ablate unwanted soft tissue and/or nerve tissue. These target tissue sites include a hernia, a fissure, a tear, a bulge of the intervertebral disc or a nerve.

In some embodiments, there is a method of providing radiofrequency treatment to an intervertebral disc, the disc comprising a nucleus pulposus, an annulus fibrosus, the method comprising: inserting an cannula up to the annulus fibrosus; inserting a needle comprising a needle tip through the cannula to penetrate the disc annulus and enter the nucleus pulposus, determining the correct depth of needle penetration using fluoroscopy or by a needle stopper disposed on the needle tip to prevent insertion beyond a target tissue site; extending a radiofrequency electrode from the needle tip to form a coil of the radiofrequency electrode within the nucleus pulposus adjacent to a target ablation site; and activating the radiofrequency electrode to deliver radiofrequency energy to the ablation site.

In accordance with some embodiments, various approaches to the site for radiofrequency ablation are contemplated. In the context of intervertebral disc treatments, in some embodiments of the invention a posterior, posterolateral, lateral, anterolateral, or anterior approach or trajectory can be used to penetrate the intervertebral disc. In some embodiments various percutaneous and non-percutaneous procedures can be used.

Any of the methods described herein can be repeated until all target tissues have been ablated. This method may be used to ablate the activities of neurons that are responsible in whole or in part for painful indications affecting bones, soft tissues, joints or a cavity. In some embodiments, two separate probes can be used simultaneously to better target and ensure more effective ablation.

In other embodiments, the methods of the present disclosure further include delivering cement and/or a polymer through a small channel, for injection at the site of the nerve and/or soft tissue destruction to provide a physically barrier at the location of the nerve destruction to prevent temporary or permanent nerve regrowth, repair and return of the pain symptoms.

In various embodiments, the barrier material utilized can be any suitable material effective to prevent or at least substantially inhibit the migration of substances that regrow tissue. Illustratively, the barrier material can comprise a biodegradable synthetic polymer, in either flowable (and potentially hardenable) or non-flowable form. Illustratively, preferred barrier materials can have a first relatively flowable state during delivery and a second relatively less flowable state after implantation. For example, the barrier material may remain in an uncured, deformable, or otherwise configurable state during introduction, and rapidly cure, become harder or solidify after being introduced. Suitable materials that may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. In some embodiments, the barrier material can be a cement.

In several embodiments, the methods disclosed herein include operatively coupling the probe to a source of navigational capability to allow easier pushing through the tissues. In various embodiments, the methods of ablation disclosed herein can include a pre-procedure step wherein the probe can be coupled to a CT or MRI machine so that the target nerve and/or soft tissue to be ablated can be identified and accurately located during the destruction procedure.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for providing radiofrequency current to a target tissue site, the device comprising:
   a cannula having a proximal end and a distal end and a longitudinal axis therebetween, the distal end comprising a tip;
   a first electrode configured to conduct and discharge radiofrequency current for heating the target tissue site, the first electrode disposed within the cannula and having a retracted position within the longitudinal axis of the cannula and a deployed position outside the tip of the cannula, the first electrode configured to have a coiled region when in the deployed position outside the tip of the cannula;
   a second electrode disposed within the cannula, wherein the second electrode has a helical configuration and is concentric with the first electrode, when the first electrode is in the deployed position;
   an adjustment member disposed at or near the proximal end of the cannula, the adjustment member configured to engage the first electrode to move the first electrode from the retracted position to the deployed position; and an insulation material disposed in or around at least a portion of the cannula, wherein when the first electrode is in the deployed position, a portion of the first electrode within the cannula remains in a straight configuration.

2. A device according to claim 1, wherein (i) the second electrode is configured to conduct radiofrequency away from the target tissue site; or (ii) the second electrode is movable in a retracted position within the longitudinal axis of the cannula and a deployed position outside the tip of the cannula.

3. A device according to claim 2, wherein the second electrode is flexible and extendable beyond the tip of the distal end of the cannula when in the deployed position and does not contact the first electrode.

4. A device according to claim 2, wherein the second electrode is rigid when urged from the cannula in the deployed position.

5. A device according to claim 2, wherein the second electrode is configured to become a coil when extended beyond the cannula, the coil being disposed within the coiled region of the first electrode.

6. A device according to claim 2, wherein the second electrode is urged from the cannula in the deployed position and becomes a coil smaller in size than the coiled region of the first electrode and is positioned adjacent to the first electrode when the first electrode is in the deployed position.

7. A device according to claim 1, wherein (i) the insulation material is disposed between the first electrode and the second electrode and configured to reduce or prevent conduction of radiofrequency current in the cannula; or (ii) the insulation material is coated on at least a portion of the first and/or second electrode.

8. A device according to claim 1, wherein the second electrode comprises Nitinol wire.

9. A device according to claim 1, wherein an outer surface of the second electrode is also coated with the insulation material.

10. A device according to claim 1, wherein the second electrode is uninsulated near the tip of the cannula.

11. A device according to claim 1, wherein the second electrode is disposed within the cannula at the proximal end of the cannula.

12. A device for providing radiofrequency current to a target tissue site, the device comprising:

a cannula having a proximal end and a distal end and a longitudinal axis therebetween, the distal end comprising a tip;

a first electrode configured to conduct and discharge radiofrequency current for heating the target tissue site, the first electrode disposed within the cannula and having a retracted position within the longitudinal axis of the cannula and a deployed position outside the tip of the cannula, the first electrode configured to have a coiled region when in the deployed position outside the tip of the cannula;

a second electrode disposed within the cannula;

an adjustment member disposed at or near the proximal end of the cannula, the adjustment member configured to engage the first electrode to move the first electrode from the retracted position to the deployed position;

an insulation material; and an electrical connection assembly configured to electrically couple the first and/or second electrode to a radiofrequency power source, wherein when the first electrode is in the deployed position, a portion of the first electrode within the cannula remains in a straight configuration, wherein the second electrode has a deployed position and when the second electrode is in the deployed position, a portion of the second electrode within the cannula is in a straight configuration and a portion of the second electrode is in a coiled configuration, and when both electrodes are in the deployed positions, the first electrode and the second electrode are parallel within the cannula and in a concentric coiled configuration outside of the cannula.

13. A device according to claim 12, wherein the cannula comprises a cooling channel configured to cool the first and/or second electrode.

14. A device according to claim 12, wherein the insulation material is disposed between the first electrode and the second electrode and configured to reduce or prevent conduction of radiofrequency current in the cannula.

* * * * *

UNITED STATES PATENT AND TRADEMARK OFFICE
CERTIFICATE OF CORRECTION

PATENT NO. : 9,895,190 B2
APPLICATION NO. : 14/263620
DATED : February 20, 2018
INVENTOR(S) : Trieu Page 1 of 1

It is certified that error appears in the above-identified patent and that said Letters Patent is hereby corrected as shown below:

In the Specification

In Column 4, Line 35, delete "refracted" and insert -- retracted --, therefor.

In Column 7, Line 67, delete "refracted" and insert -- retracted --, therefor.

In Column 12, Line 50, delete "distal end 131." and insert -- distal end 135. --, therefor.

In Column 14, Line 15, delete "hosing 100" and insert -- device housing 100 --, therefor.

In Column 16, Line 41, delete "Referring to FIG. 8, FIGS. 8A-8J," and insert -- Referring to FIGS. 8A-8J, --, therefor.

Signed and Sealed this
Twenty-first Day of August, 2018

Andrei Iancu
*Director of the United States Patent and Trademark Office*